United States Patent
Low et al.

(10) Patent No.: US 11,406,697 B2
(45) Date of Patent: *Aug. 9, 2022

(54) METHODS AND COMPOSITIONS FOR TREATING GLIOMA AND MEDULLOBLASTOMA BRAIN TUMORS USING THE ZIKA VIRUS

(71) Applicant: REGENTS OF THE UNIVERSITY OF MINNESOTA, Minneapolis, MN (US)

(72) Inventors: Walter C. Low, Minneapolis, MN (US); Maple Shiao, Minneapolis, MN (US); Andrew Crane, Minneapolis, MN (US); Christopher J. Sipe, Minneapolis, MN (US); Clairice Pearce, Minneapolis, MN (US); Joseph Voth, Minneapolis, MN (US); Nikolas Toman, Minneapolis, MN (US); Craig Bierle, Minneapolis, MN (US); Matthew Chrostek, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/808,701

(22) Filed: Mar. 4, 2020

(65) Prior Publication Data

US 2020/0345826 A1 Nov. 5, 2020

Related U.S. Application Data

(63) Continuation of application No. 16/116,426, filed on Aug. 29, 2018, now Pat. No. 10,610,583.

(60) Provisional application No. 62/552,934, filed on Aug. 31, 2017.

(51) Int. Cl.
*A61K 39/12* (2006.01)
*A61K 9/00* (2006.01)
*A61P 35/00* (2006.01)
*A61K 39/00* (2006.01)

(52) U.S. Cl.
CPC ........... *A61K 39/12* (2013.01); *A61K 9/0019* (2013.01); *A61P 35/00* (2018.01); *A61K 2039/585* (2013.01); *C12N 2770/24134* (2013.01)

(58) Field of Classification Search
CPC ........... A61K 2300/00; A61K 38/1709; A61K 45/06; A61K 39/12; A61K 9/0019; A61K 2039/585; A61K 35/768; A61P 35/00; C07K 14/005; C12N 2740/16322; C12N 2770/24134; C12N 2750/14143; G01N 33/5011

See application file for complete search history.

(56) References Cited

U.S. PATENT DOCUMENTS

| | | | |
|---|---|---|---|
| 7,964,186 B2 | 6/2011 | Coffey | |
| 8,309,531 B2 | 11/2012 | Turner | |
| 10,610,583 B2 * | 4/2020 | Low | A61K 9/0019 |
| 2015/0299271 A1 | 10/2015 | Russell | |

FOREIGN PATENT DOCUMENTS

| | | |
|---|---|---|
| WO | 2001019380 | 3/2001 |
| WO | 2018035294 | 2/2018 |

OTHER PUBLICATIONS

Ahmed N, et al. HER2-Specific T Cells Target Primary Glioblastoma Stem Cells and Induce Regression of Autologous Experimental Tumors. 2010. doi: 10.1158/1078-0432.CCR-09-1322.

Ahmed N, et al. Regression of Experimental Medulloblastoma following Transfer of HER2-Specific T Cells. 2007. do:i 10.1158/0008-5472.CAN-06-4309.

Alemany R, et al. Replicative adenoviruses for cancer therapy. Nat Biotechnol. 2000;18(7):723-7. Epub Jul. 11, 2000. doi: 10.1038/77283. PubMed PMID: 10888838.

Amano S, et al. Tumoricidal bystander effect in the suicide gene therapy using mesenchymal stem cells does not injure normal brain tissues. Cancer Lett. 2011;306(1):99-105. Epub Apr. 1, 2011. doi: 10.1016/j.canlet.2011.02.037. PubMed PMID: 21450400.

Babu R AD. Rindopepimut: an evidence-based review of its therapeutic potential in 2012. doi: 10.2147/CE.S29001.

Barba, D. et al. Intratumoral LAK cell and interleukin-2 therapy of human gliomas. http://dxdoiorg/103171/ins19897020175. 1989. doi: 10.3171/Ins.1989.70.2.0175.

Barkovich, A.J., et al. A developmental and genetic classification for malformations of cortical development: update 2012.

Bhattacharyya, S., et al. (2013). Enveloped Viruses Disable Innate Immune Responses in Dendritic Cells by Direct Activation of TAM Receptors. Cell Host Microbe. 2013, 14 (2) pp. 136-147.

Bielamowicz KJ, et al. Adoptive Cell Therapies for Glioblastoma. Cancer Genetics. 2013;3. doi: 10.3389/fonc.2013.00275.

Boiardi A, Besta, et al. Loco-regional immunotherapy with recombinant interleukin-2 and adherent lymphokine-activated killer cells (A-LAK) in recurrent glioblastoma patients. Cancer Immunology, Immunotherapy. 2013;39(3):193-7.

Bond, J., et al. (2005). A centrosomal mechanism involving CDK5RAP2 and CENPJ controls brain size. Nat. Genet. 37, 353-355.

Bowen, J.R., et al. (2017). Zika Virus Antagonizes Type I Interferon Responses during Infection of Human Dendritic Cells. PLoS Pathog. 13, e1006164.

Broder H, et al. MART-1 adenovirus-transduced dendritic cell immunization in a murine model of metastatic central ervous system tumor. Journal of Neuro-Oncology. 2014;64(1-2):21-30. doi: 10.1007/BF02700017.

(Continued)

*Primary Examiner* — Bao Q Li
(74) *Attorney, Agent, or Firm* — Quarles & Brady LLP

(57) ABSTRACT

In one embodiment, the present invention is a method of treating glioma and medulloblastoma brain tumors using the Zika virus and a tumor vaccine.

23 Claims, 11 Drawing Sheets

(56) References Cited

OTHER PUBLICATIONS

Bulstrode, H., et al. Elevated FOXG1 and SOX2 in glioblastoma enforces neural stem cell identity through transcriptional control of cell cycle and epigenetic regulators. Genes & development 31.8 (2017): 757-773.
Campbell SA, et al. Genetic Determinants of Cell Type-Specific Poliovirus Propagation in HEK 293 Cells. J Virol. 79 (2005). p. 6281-6290.
Cao-Lormeau VM, et al. Guillain-Barré Syndrome outbreak associated with Zika virus infection in French Polynesia a case-control study. Lancet. Apr. 9, 2016;387(10027):1531-9.
Caruso Denise A. et al. Results of a phase 1 study utilizing monocyte-derived dendritic cells pulsed with tumor RNA.
Castle JC, et al. Exploiting the Mutanome for Tumor Vaccination. Cancer research 72.5 (2012): 1081-1091.
Castriconi R, et al. NK Cells Recognize and Kill Human Glioblastoma Cells with Stem Cell-Like Properties. 2009. doi: 10.4049/jimmunol.0802845.
CELLDEX Therapeutics. Data Safety and Monitoring Board Recommends Celldex's Phase 3 Study of RINTEGA® (rindopepimut) in Newly Diagnosed Glioblastoma be Discontinued as it is Unlikely to Meet Primary Overall Survival Endpoint in Patients with Minimal Residual Disease (NASDAQ:CLDX) [Internet]. Mar. 7, 2016. Available from: http://r.celldex.com/releasedetail.cfm?ReleaseID=959021.
Chaffey, N. Molecular biology of the cell by Alberts, B. et al. Book Review. 4th edn. Ann Bot. 2003;91(3):401. doi: 10.1093/aob/mcg023. PubMed Central PMCID: PMC4244961.
Chakraborty, S. (2016). Computational analysis of perturbations in the post-fusion Dengue virus envelope protein highlights known epitopes and conserved residues in the Zika virus. F1000Research 5, 1150.
Chang SM, et al. Phase II study of CCI-779 in patients with recurrent glioblastoma multiforme. Invest New Drugs. 2005;23(4):357-61. Epub Jul. 14, 2005. doi: 10.1007/s10637-005-1444-0. PubMed PMID: 16012795.
Cheever MA, et al. The Prioritization of Cancer Antigens: A National Cancer Institute Pilot Project for the Acceleration of Translational Research. 2009. doi: 10.1158/1078-0432.CCR-09-0737.
Chiocca EA, et al. Phase IB Study of Gene-Mediated Cytotoxic Immunotherapy Adjuvant to Up-Front Surgery and intensive Timing Radiation for Malignant Glioma. 2011. doi: 10.1200/JCO.2011.35.5222.
Chiocca, E. A., et al. "A phase I open-label, dose-escalation, multi-institutional trial of injection with an E1B-Attenuated adenovirus, ONYX-015, into the peritumoral region of recurrent malignant gliomas, in the adjuvant setting." Molecular Therapy 10.5 (2004): 958-966.
Chmielewski M, et al. Antigen-Specific T-Cell Activation Independently of the MHC: Chimeric Antigen Receptor—Redirected T Cells. Front Immunol. 2013;4. doi: 10.3389/fimmu.2013.00371. PubMed PMID: 24273543; PubMed Central PMCID: PMC3822734.
Choi BD, et al. (2009) EGFRvIII-Targeted Vaccination Therapy of Malignant Glioma. Brain Pathology.19(4)713-23. doi: 10.1111/j.1750-3639.2009.00318.x.
Choi BD, et al. Intracerebral delivery of a third generation EGFRvIII-specific chimeric antigen receptor is efficacious against human glioma. J Clin Neurosci. 2014;21(1):189-90. Epub Sep. 24, 2013. doi: 10.1016/j.jocn.2013.03.012. PubMed PMID: 24054399; PubMed Central PMCID: PMCPMC3867597.
Cizmecioglu, O., et al. (2010). Cep152 acts as a scaffold for recruitment of Plk4 and CPAP to the centrosome. J. Cell Biol. 191.
Coutard, B., et al. (2017). Zika Virus Methyltransferase: Structure and Functions for Drug Design Perspectives. J. Virol. 91, e02202-16.
Cross D, et al. Gene Therapy for Cancer Treatment: Past, Present and Future. 2006. doi: 10.3121/cmr.4.3.218.

Cunha, M.S., et al. (2016). First Complete Genome Sequence of Zika Virus (Flaviviridae, Flavivirus) from an Autochthonous Transmission in Brazil. Genome Announc. 4, e00032-16.
Curtin SC, et al. Declines in Cancer Death Rates Among Children and Adolescents in the United States, 1999-2014. NCHS Data Brief. Sep. 2016;(257):1-8. PubMed PMID: 27648773.
Dang, J., et al. (2016). Zika Virus Depletes Neural Progenitors in Human Cerebral Organoids through Activation of the Innate Immune Receptor TLR3. Cell stem cell 19.2 (2016): 258-265.
Dick, G. W., et al. Zika virus. I. Isolations and serological specificity. Trans. R. Soc. Trop. Med. Hyg 46, 509-520 (1952).
Dillman RO, et al. Intracavitary Placement of Autologous Lymphokine-Activated Killer (LAK) Cells after Resection of Recurrent Glioblastoma. Journal of Immunotherapy. 2004;27(5):398-44.
Dimeco F, et al. Paracrine delivery of IL-12 against intracranial 9L gliosarcoma in rats. J Neurosurg. 2000;92(3):419-27. Epub Mar. 4, 2000. doi: 10.3171/jns.2000.92.3.0419. PubMed PMID: 10701528.
Dobrikova EY, et al. Recombinant oncolytic poliovirus eliminates glioma in vivo without genetic adaptation to a pathogenic phenotype. Mol Ther. 2008;16(11):1865-72. doi: 10.1038/mt.2008.184. PubMed PMID: 18766173; PubMed Central PMCID: PMC2856473.
Dorig RE, et al. The human CD46 molecule is a receptor for measles virus (Edmonston strain). Cell. 1993;75(2):295-305. Epub Oct. 22, 1993. PubMed PMID: 8402913.
Dos Santos T, et al. Zika Virus and the Guillain-Barre Syndrome—Case Series from Seven Countries. N Engl J Med. Aug. 31, 2016. [Epub ahead of print].
Dranoff, Glenn. "GM-CSF-based cancer vaccines." Immunological reviews 188.1 (2002): 147-154.
Driessche AV, et al. Active Specific Immunotherapy Targeting the Wilms' Tumor Protein 1 (WT1) for Patients with Hematological Malignancies and Solid Tumors: Lessons from Early Clinical Trials. 2012. doi: 10.1634/theoncologist.2011-0240.
Duffy MR, et al. Zika virus outbreak on Yap Island, Federated States of Micronesia. N Engl J Med. Jun. 11, 2009;360 (24):2536-43.
Ehtesham M, et al. The use of interleukin 12-secreting neural stem cells for the treatment of intracranial glioma. Cancer Res. 2002;62(20):5657-63. Epub Oct. 18, 2002. PubMed PMID: 12384520.
Etcheverry A, et al. DNA methylation in glioblastoma: impact on gene expression and clinical outcome. BMC Genomics. 2010;11(1):701. doi: 10.1186/1471-2164-11-701.
Feller S. Poliovirus therapy against cancer given 'breakthrough' status by FDA2016. May 17, 2016. Available from http://www.upi.com/Health_News/2016/05/17/Poliovirus-therapy-against-cancer-given-breakthrough-status-by-FDA/6541463499960/.
Fong B, et al. Monitoring of Regulatory T Cell Frequencies and Expression of CTLA-4 on T Cells, before and after DC Vaccination, Can Predict Survival in GBM Patients. Plos One. 2012;7(4). doi: 10.1371/journal.pone.0032614.
Frayling, T.M., et al. (2007). A Common Variant in the FTO Gene Is Associated with Body Mass Index and Predisposes to Childhood and Adult Obesity. Science (80-.). 316.
Fukuhara, H., et al. "Oncolytic virus therapy: A new era of cancer treatment at dawn." Cancer science 107.10 (2016): 1373-1379.
Gabriel, E., et al. Recent Zika Virus Isolates Induce Premature Differentiation of Neural Progenitors in Human Brain Organoids. Cell Stem Cell 2017, 20 (3), 397-406.
Galanis E, et al. Phase II Trial of Temsirolimus (CCI-779) in Recurrent Glioblastoma Multiforme: A North Central Cancer Treatment Group Study. 2005. doi: 10.1200/JCO.2005.23.622.
Galanis E, et al. Use of viral fusogenic membrane glycoproteins as novel therapeutic transgenes in gliomas. Hum Gene Ther. 2001;12(7):811-21. Epub May 8, 2001. doi: 10.1089/104303401750148766. PubMed PMID: 11339897.
Gerlinger M, et al. Intratumor heterogeneity and branched evolution revealed by multiregion sequencing. N Engl J Med. 2012;366(10):883-92. Epub Mar. 9, 2012. doi: 10.1056/NEJMoa1113205. PubMed PMID: 22397650.
Germano IM, et al. Adenovirus/Herpes Simplex—Thymidine Kinase/Ganciclovir Complex: Preliminary Results of a Phase I trial in Patients with Recurrent Malignant Gliomas. Journal of Neuro-Oncology. 2003;65(3). Epub 289. doi: 10.1023/B:NEON.0000003657.95085.56.

(56) References Cited

OTHER PUBLICATIONS

Goetz, C. et al. "Preparing an oncolytic poliovirus recombinant for clinical application against glioblastoma multiforme." Cytokine & growth factor reviews 21.2-3 (2010): 197-203.
Grant, A., et al. (2016). Zika Virus Targets Human STAT2 to Inhibit Type I Interferon Signaling. Cell host & microbe 19.6 (2016): 882-890.
Gromeier M, et al. Expression of the human poliovirus receptor/CD155 gene during development of the central nervous system: implications for the pathogenesis of poliomyelitis. Virology. 2000;273(2):248-57. Epub Aug. 1, 2000. doi: 10.1006/viro.2000.0418. PubMed PMID: 10915595.
Gromeier M, et al. Intergeneric poliovirus recombinants for the treatment of malignant glioma. Proc Natl Acad Sci U S A. 2000;97(12):6803-8. Epub Jun. 7, 2000. PubMed PMID: 10841575; PubMed Central PMCID: PMCPMC18745.
Gromeier M, et al. Internal ribosomal entry site substitution eliminates neurovirulence in intergeneric poliovirus Yecombinants. Proc Natl Acad Sci USA. 1996;93(6):2370-5. Epub Mar. 19, 1996. PubMed PMID: 8637880; PubMed Central PMCID: PMCPMC39803.
Guernsey, D.L., et al. (2010). Mutations in Centrosomal Protein CEP152 in Primary Microcephaly Families Linked to MCPH4. The American Journal of Human Genetics 87.1 (2010): 40-51.
Hamel R, et al. Biology of Zika Virus Infection in Human Skin Cells. J Virol. Sep. 2015;89(17):8880-96. doi: 10.1128/JVI.00354-15. Epub Jun. 17, 2015.
Han J, et al. CAR-Engineered NK Cells Targeting Wild-Type EGFR and EGFRvIII Enhance Killing of Glioblastoma and Patient-Derived Glioblastoma Stem Cells. Sci Rep. 2015;5:11483. Epub Jul. 15, 2015. doi: 10.1038/srep11483. PubMed PMID: 26155832; PubMed Central PMCID: PMCPMC4496728.
Hayes RL, et al. Improved long term survival after intracavitary interleukin-2 and lymphokine-activated killer cells for adults with recurrent malignant glioma. 1995. Cancer.76(5):840-52. doi: 10.1002/1097-0142(19950901)76:5<840::AID-CNCR2820760519>3.0 CO;2-R.
Hegde M, et al. Combinational Targeting Offsets Antigen Escape and Enhances Effector Functions of Adoptively Transferred T Cells in Glioblastoma. Molecular Therapy. 2013;21(11):2087-101. doi: doi:10.1038/mt.2013.185.
Heimberger AB, et al. Bone marrow-derived dendritic cells pulsed with tumor homogenate induce immunity against syngeneic intracerebral glioma. Journal of Neuroimmunology. 2000;103(1):16-25. PubMed PMID: 10674985.
Heimberger AB, et al. Epidermal Growth Factor Receptor VIII Peptide Vaccination Is Efficacious against Established Intracerebral Tumors. Clinical cancer research 9.11 (2003): 4247-4254.
Heymann, D.L., et al. (2016). Zika virus and microcephaly: why is this situation a PHEIC? Lancet 387, 719-721.
Hinrichs CS, et al. Reassessing target antigens for adoptive T-cell therapy. Nature Biotechnology. 2013;31:999-1008. doi: doi:10.1038/nbt.2725.
Hu, J.K.-H., et al. (2017). An FAK-YAP-mTOR Signaling Axis Regulates Stem Cell-Based Tissue Renewal in Mice. Cell Stem Cell.
Immonen A, et al. AdvHSV-tk Gene Therapy with Intravenous Ganciclovir Improves Survival in Human Malignant Glioma: A Randomised, Controlled Study. Molecular Therapy. 2004;10(5):967-72. doi: doi:10.1016/j.ymthe.2004.08.002.
Ivics Z, et al. Molecular reconstruction of Sleeping Beauty, a Tc1-like transposon from fish, and its transposition in human cells. Cell. 1997;91(4):501-10. Epub Dec. 9, 1997. PubMed PMID: 9390559.
Iyer G, et al. Genome Sequencing Identifies a Basis for Everolimus Sensitivity. 2012. doi: 10.1126/science.1226344.
Jabado, N., et al. (2000). Natural Resistance to Intracellular Infections. J. Exp. Med. 192.
Jacobs SK, et al. Interleukin-2 or Autologous Lymphokine-activated Killer Cell Treatment of Malignant Glioma: Phase I Trial. 1986. Cancer research 46.4 Part 2 (1986): 2101-2104.

Jean WC, et al. Effects of combined granulocyte-macrophage colony-stimulating factor (GM-CSF), interleukin-2, and interleukin-12 based immunotherapy against intracranial glioma in the rat. J Neurooncol. 2004;66(1-2):39-49. Epub Mar. 16, 2004. PubMed PMID: 15015768.
Jean WC, et al. Interleukin-12-based immunotherapy against rat 9L glioma. Neurosurgery. 1998;42(4):850-6; discussion 6-7. Epub May 9, 1998. PubMed PMID: 9574650.
Jia, G., et al. (2011). N6-Methyladenosine in nuclear RNA is a major substrate of the obesity-associated FTO. Nature chemical biology 7.12 (2011): 885.
Johnson LA, et al. Chimeric antigen receptor engineered T cells can eliminate brain tumors and initiate long-term protection against recurrence. Oncoimmunology. Oncoimmunology 3.7 (2014).
Johnson LA, et al. Rational development and characterization of humanized anti-EGFR variant III chimeric antigen receptor T cells for glioblastoma. Sci Transl Med. 2015;7(275):275ra22. Epub Feb. 20, 2015. doi: 10.1126/scitranslmed.aaa4963 PubMed PMID: 25696001; PubMed Central PMCID: PMCPMC4467166.
Jurianz K, et al. Complement resistance of tumor cells: basal and induced mechanisms. Mol Immunol. 1999;36 (13-14):929-39. Epub Mar. 4, 2000. PubMed PMID: 10698347.
Katakura R, et al. Therapeutic Efficacy of Adoptive Cell Transfer on Survival of Patients with Glioblastoma Multiforme: Case Reports. Case Reports in Oncology. 2010;3(2):110-24. PubMed PMID: 20740183.
Kebriaei P, et al. First Clinical Trials Employing Sleeping Beauty Gene Transfer System and Artificial Antigen Presenting Cells To Generate and Infuse T Cells Expressing CD19-Specific Chimeric Antigen Receptor. Blood 2013 122:166.
Kikuchi T, et al. Anti-tumor activity of interleukin-2-producing tumor cells and recombinant interleukin 12 against mouse glioma cells located in the central nervous system. Int J Cancer. 1999;80(3):425-30. Epub Feb. 6, 1999. PubMed PMID :9935185.
Kim, S.Y., et al. (2017). Interaction of Zika Virus Envelope Protein with Glycosaminoglycans. Biochemistry 56, 1151-1162.
Kim, W. et al. "Dendritic cell vaccines for brain tumors." Neurosurgery Clinics 21.1 (2010): 139-157.
Kleber De Oliveira, W., et al. (2016). Increase in Reported Prevalence of Microcephaly in Infants Born to Women Living in Areas with Confirmed Zika Virus Transmission During the First Trimester of Pregnancy—Brazil, 2015. MMWR. Morb. Mortal. Wkly. Rep. 65.
Kong S, et al. Suppression of Human Glioma Xenografts with Second-Generation IL13R-Specific Chimeric Antigen Receptor—Modified T Cells. 2012. doi: 10.1158/1078-0432.CCR-12-0319.
Krogan NJ ea. The Cancer Cell Map Initiative: Defining the Hallmark Networks of Cancer. Molecular cell 58.4 (2015): 690-698.
Kuriyama S, et al. Cancer gene therapy with HSV-tk/GCV system depends on t-cell-mediated immune responses and causes apoptotic death of tumor cells In vivo. International Journal of Cancer. 1999 83(3):374-80.
Kurzrock R, et al. Precision Oncology for Patients with Advanced Cancer: The Challenges of Malignant Snowflakes. Cell Cycle. 2015:0. Epub Jun. 2, 2015. doi: 10.1080/15384101.2015.1041695. PubMed PMID: 26030337.
Landi D, et al. Human Cytomegalovirus Antigens in Malignant Gliomas as Targets for Adoptive Cellular Therapy. Frontiers in Oncology. 2014;4. doi: 10.3389/fonc.2014.00338.
Le Mercier M, et al. A simplified approach for the molecular classification of glioblastomas. PLoS One. 2012;7(9) e45475. Epub Oct. 3, 2012. doi: 10.1371/journal.pone.0045475. PubMed PMID: 23029035; PubMed Central PMCID: PMCPmc3445522.
Lee EQ, et al. Phase I/II study of sorafenib in combination with temsirolimus for recurrent. Neuro Oncol. 2012;14 (12):1511-8. Epub Oct. 27, 2012. doi: 10.1093/neuonc/nos264. PubMed PMID: 23099651; PubMed Central PMCID: PMCPmc3499017.
Levitan D. Polio-Rhinovirus Conjugate Shows Promise in Early Recurrent Glioblastoma Trial. Nov. 17, 2014. Available from: http://www.cancernetwork.com/sno-2014/polio-rhinovirus-conjugate-shows-promise-early-recurrent-glioblastoma-trial.
Li S, et al. Bystander effect in glioma suicide gene therapy using bone marrow stromal cells. Stem Cell Res. 2012;9(3):270-6. Epub Oct. 2, 2012. doi: 10.1016/j.scr.2012.08.002. PubMed PMID: 23022734.

(56) References Cited

OTHER PUBLICATIONS

Li, H, et al. (2016). Zika Virus Infects Neural Progenitors in the Adult Mouse Brain and Alters Proliferation. Cell stem cell 19.5 (2016): 593-598.

Li, L. et al. A Phase II study of anti-epidermal growth factor receptor radioimmunotherapy in the treatment of glioblastoma multiforme. http://dxdoiorg/103171/20102JNS091211.2010. doi: 2010.2.JNS091211.

Sampson JH, et al. Tumor-specific immunotherapy targeting the EGFRvIII mutation in patients with malignant glioma 2008;20(5):267-75. doi: 10.1016/j.smim.2008.04.001.

Samuels, Y. et al. Oncogenic PI3K and its role in cancer. Curr. Opin. Oncol. 18, 77-82 (2006).

Sankhla SK, et al. Adoptive immunotherapy using lymphokine-activated killer (LAK) cells and interleukin-2 for recurrent malignant primary brain tumors. Journal of Neuro-Oncology. 2013;27(2):133-40.

Schuessler A, et al. Autologous T-cell Therapy for Cytomegalovirus as a Consolidative Treatment for Recurrent Glioblastoma. 2014. doi: 10.1158/0008-5472.CAN-14-0296.

Sequist LV, et al. Genotypic and Histological Evolution of Lung Cancers Acquiring Resistance to EGFR Inhibitors. 2011. doi: 10.1126/scitranslmed.3002003.

Sgubin D, et al. Oncolytic herpes simplex virus counteracts the hypoxia-induced modulation of glioblastoma stem-like cells. Stem Cells Transl Med. 2012;1(4):322-32.

Shen C-J, et al. Chimeric antigen receptor containing ICOS signaling domain mediates specific and efficient antitumor effect of T cells against EGFRvIII expressing glioma. 2013. doi: 10.1186/1756-8722-6-33.

Shiina S, et al. CAR T Cells Targeting Podoplanin Reduce Orthotopic Glioblastomas in Mouse Brains. Cancer Immunol Res. 2016;4(3):259-68.

Singh H, et al. A new approach to gene therapy using Sleeping Beauty to genetically modify clinical-grade T cells to target CD19. Immunological reviews 257.1 (2014): 181-190.

Soares De Oliveira-Szejnfeld P, et al. Congenital Brain Abnormalities and Zika Virus: What the Radiologist Can Expect to See Prenatally and Postnatally. Radiology. Aug. 23, 2016:161584.[Epub ahead of print].

Song, M. S., et al. The functions and regulation of the PTEN tumour suppressor. Nature Rev. Mol. Cell Biol. 13, 283-296 (2012).

Souza, B.S.F., et al. (2016). Zika virus infection induces mitosis abnormalities and apoptotic cell death of human neural progenitor cells. Sci. Rep. 6, 39775.

Stephen, P., et al. (2016). Structural Insight into NS5 of Zika Virus Leading to the Discovery of MTase Inhibitors. J. Am. Chem. Soc. 138, 16212-16215.

Stieber D, et al. Glioblastomas are composed of genetically divergent clones with distinct tumourigenic potential and variable stem cell-associated phenotypes. Acta Neuropathol. 2014;127(2):203-19.

Tang, H., et al. (2016). Zika Virus Infects Human Cortical Neural Progenitors and Attenuates Their Growth. Cell stem cell 18.5 (2016): 587-590.

Thaci B, et al. Significance of interleukin-13 receptor alpha 2-targeted glioblastoma therapy. Neuro-oncology 16.10 (2014): 1304-1312.

Toth K, et al. Oncolytic (replication-competent) adenoviruses as anticancer agents. Expert Opin Biol Ther. 2010;10 (3):353-68.

Verhaak RGW, et al. Integrated Genomic Analysis Identifies Clinically Relevant Subtypes of Glioblastoma Characterized by Abnormalities in PDGFRA, IDH1, EGRF, and NF1. Cancer cell 17.1 (2010): 98-110.

Wallenfriedman MA, et al. Effects of continuous localized infusion of granulocyte-macrophage colony-stimulating actor and inoculations of irradiated glioma cells on tumor regression. J Neurosurg. 1999;90(6): 1064-71.

Wells, M.F., et al. Genetic Ablation of AXL Does Not Protect Human Neural Progenitor Cells and Cerebral Organoids from Zika Virus Infection. Cell stem cell 19.6 (2016): 703-708.

Wen PY, et al. Malignant Gliomas in Adults. The New England Journal of Medicine. 2008;359(5):492-507.

Wheler J, et al. Unique molecular landscapes in cancer: implications for individualized, curated drug combinations. Cancer Res. 2014;74(24):7181-4.

Wohlfahrt ME, et al. A capsid-modified, conditionally replicating oncolytic adenovirus vector expressing Trail Leads to enchanced cancer cell killing in human glioblastoma models. Cancer Res. 2007;67(18):8783-90.

Wollmann G, et al. Oncolytic virus therapy for glioblastoma multiforme: concepts and candidates. Cancer J. Jan.-Feb. 2012; 18(1):69-81.

Wu A, et al. Persistence of CD133+ Cells in Human and Mouse Glioma Cell Lines: Detailed Characterization of GL261 Glioma Cells with Cancer Stem Cell-Like Properties. Stem cells and development 17.1 (2008): 173-184.

Wu AH, et al. Identification of EGFRvIII-derived CTL epitopes restricted by HLA A0201 for dendritic cell based Immunotherapy of gliomas. J. Neurooncool. 2006;76(1):23-30.

Yaghoubi SS, et al. Noninvasive detection of therapeutic cytolytic T cells with 18F-FHBG PET in a patient with glioma. Nat Clin Pract Oncol. 2009;6(1):53-8.

Yamanaka R, et al. Vaccination of recurrent glioma patients with tumour lysate-pulsed dendritic cells elicits immune responses: results of a clinical phase I/II trial. British Journal of Cancer. 2003;89(7):1172-9.

Yan X, et al. A CD133-related gene expression signature identifies an aggressive glioblastoma subtype with excessive nutations. Proceedings of the National Academy of Sciences 108.4 (2011): 1591-1596.

Yu JS, et al. Vaccination of Malignant Glioma Patients with Peptide-pulsed Dendritic Cells Elicits Systemic Cytotoxicity and Intracranial T-cell Infiltration. Cancer res 61 (2001): 842-847.

Yu JS, et al. Vaccination with Tumor Lysate-Pulsed Dendritic Cells Elicits Antigen-Specific, Cytotoxic T-Cells in Patients with Malignant Glioma. 2004. Cancer research 64.14 (2004): 4973-4979.

Zhang C, et al. ErbB2/HER2-Specific NK Cells for Targeted Therapy of Glioblastoma. Journal of the National Cancer Institute 108.5 (2015): djv375.

Zhang F, et al. Molecular signatures associated with ZIKV exposure in human cortical neural progenitors. Nucleic Acids Res. Aug. 31, 2016. pii: gkw765.

Zheng, G., et al. ALKBH5 Is a Mammalian RNA Demethylase that Impacts RNA Metabolism and Mouse Fertility. Molecular cell 49.1 (2013): 18-29.

Zhu, Z., et al. "Zika virus has oncolytic activity against glioblastoma stem cells." Journal of Experimental Medicine 214.10 (2017): 2843-2857.

Zinn PO, et al. A novel volume-age-KPS (VAK) glioblastoma classification identifies a prognostic cognate microRNA-gene signature. PLoS One. 2012;7(8):e41522. Epub Aug. 8, 2012. doi: 10.1371/journal.pone.0041522. PubMed PMID: 22870228; PubMed Central PMCID: PMCPmc3411674.

Knutson, K. L., et al. "Tumor antigen-specific T helper cells in cancer immunity and immunotherapy." Cancer Immunology, Immunotherapy 54.8 (2005): 721-728.

Liang, Q., et al. (2016). Zika Virus NS4A and NS4B Proteins Deregulate Akt-mTOR Signaling in Human Fetal Neural Stem Cells to Inhibit Neurogenesis and Induce Autophagy. Cell stem cell 19.5 (2016): 663-671.

Liau LM, et al. Dendritic Cell Vaccination in Glioblastoma Patients Induces Systemic and Intracranial T-cell Responses Modulated by the Local Central Nervous System Tumor Microenvironment. 2005. doi: 10.1158/1078-0432.CCR-05-0464.

Liau, Linda M. et al. Treatment of a glioblastoma patient by vaccination with autologous dendritic cells pulsed with allogeneic major histocompatibility complex class I—matched tumor peptides. http://dxdoiorg/103171/foc2000969.2007. doi: FOC.2000.9.6.9.

Liau, Linda M. et al. Treatment of intracranial gliomas with bone marrow—derived dendritic cells pulsed with tumor antigens. J Neurosurg. 1999 vol. 90 (6), pp. 1115-1124.

Lichinchi, G., et al. (2016). Dynamics of Human and Viral RNA Methylation during Zika Virus Infection. Cell host & microbe 20.5 (2016): 666-673.

(56) References Cited

OTHER PUBLICATIONS

Lillehei KO, et al. Long-term follow-up of patients with recurrent malignant gliomas treated with adjuvant adoptive Immunotherapy. Neurosurgery. 1991;28(1):16-23. Epub Jan. 1, 1991. PubMed PMID: 1994273.
Lindenbach, B.D., et al. (2003). Molecular biology of flaviviruses. Adv. Virus Res. 59, 23-61.
Lindstedt, Ingrid, et al. "The WT1 gene—its role in tumourigenesis and prospects for immunotherapeutic advances." in vivo 28.5 (2014): 675-681.
Liu G, et al. HER-2, gp100, and MAGE-1 Are Expressed in Human Glioblastoma and Recognized by Cytotoxic T Cells. Cancer Res. 2004, 64 (14), pp. 4980-4986).
Liu Y, et al. Time course analysis and modulating effects of established brain tumor on active-specific immunotherapy. Neurosurg Focus. 2000;9(6):e3. Epub Jul. 5, 2006. PubMed PMID: 16817686. Neurosurg Focus, 2000, 9(6), pp.
Lotan, M., et al. "Cross talk between the immune system and the nervous system in response to injury: implications or regeneration." The FASEB Journal 8.13 (1994): 1026-1033.
Lui, V. W. et al. Frequent mutation of the PI3K pathway in head and neck cancer defines predictive biomarkers. Cancer Discov. 3, 761-769 (2013).
Maiti S, et al. Sleeping Beauty system to redirect T-cell specificity for human applications. Journal of immunotherapy 36.2(2013): 112.
Meertens, L., et al. Axl Mediates ZIKA Virus Entry in Human Glial Cells and Modulates Innate Immune Responses. Cell reports 18.2 (2017): 324-333.
Meertens, L., et al. The TIM and TAM Families of Phosphatidylserine Receptors Mediate Dengue Virus Entry. Cell host & microbe 12.4 (2012): 544-557.
Merrill MK, et al. Poliovirus receptor CD155-targeted oncolysis of glioma. Neuro Oncol. 2004;6(3):208-17.
Miao H, et al. EGFRvIII-Specific Chimeric Antigen Receptor T Cells Migrate to and Kill Tumor Deposits Infiltrating the Brain Parenchyma in an Invasive Xenograft Model of Glioblastoma. 2014. doi: 10.1371/journal.pone.0094281.
Miller, E., et al. Probable Zika virus-associated Guillain-Barré syndrome: Challenges with clinico-laboratory diagnosis. Journal of the neurological sciences 375 (2017): 367-370.
Modis, Y., et al. Structure of the dengue virus envelope protein after membrane fusion. Nature 427.6972 (2004): 313.
Morgan RA, et al. Recognition of Glioma Stem Cells by Genetically Modified T Cells Targeting EGFRvIII and Development of Adoptive Cell Therapy for Glioma. 2012. doi: 10.1089/hum.2012.041.
Morgan, R. A., et al. "Cancer regression and neurologic toxicity following anti-MAGE-A3 TCR gene therapy." Journal of immunotherapy 36.2 (2013): 133.
Nakai R, et al. Overexpression of Necl-5 correlates with unfavorable prognosis in patients with lung adenocarcinoma. Cancer Sci. 2010;101(5):1326-30.
Namba H, et al. Use of genetically engineered stem cells for glioma therapy. Oncol Lett. Nov. 2016. p. 9-15.
Ni HT, et al. Immunization with dendritic cells pulsed with tumor extract increases survival of mice bearing intracranial gliomas. J Neurooncol. 2001;51(1):1-9. Epub May 15, 2001. PubMed PMID: 11349874.
Ni HT, et al. Visualization of antigen-specific T cell activation in vivo in response to intracerebral administration of a xenopeptide. Exp Neurol. 164. United States: 2000 Academic Press.; 2000. p. 362-370.
Noushmehr H, et al. Identification of a CpG island methylator phenotype that defines a distinct subgroup of glioma. Cancer Cell. 2010;17(5):510-22. Epub Apr. 20, 2010. doi: 10.1016/j.ccr.2010.03.017. PubMed PMID: 20399149; PubMed Central PMCID: PMCPmc2872684.
Nowakowski, T.J., et al. (2016). Expression Analysis Highlights AXL as a Candidate Zika Virus Entry Receptor in Neural Stem Cells. Cell stem cell 18.5 (2016): 591-596.

Oehler, E., et al. (2014). Zika virus infection complicated by Guillain-Barré syndrome—case report, French Polynesia, Dec. 2013. Eurosurveillance 19, 20720.
Ostrand-Rosenberg S. Immune surveillance: a balance between protumor and antitumor immunity. 2008;18(1):11-8. doi: 10.1016/j.gde.2007.12.007.
Ostrom QT, et al. The epidemiology of glioma in adults: a "state of the science" review. Neuro Oncol. Jul. 2014; 16(7):896-913.
Phuong LK, et al. Use of a vaccine strain of measles virus genetically engineered to produce carcinoembryonic antigen as a novel therapeutic agent against glioblastoma multiforme. Cancer Res. 2003;63(10):2462-9. Epub May 17, 2003. PubMed PMID: 12750267.
Plautz GE, et al. T Cell Adoptive Immunotherapy of Newly Diagnosed Gliomas. Clinical Cancer Research 6.6 (2000): 2209-2218.
Prins RM, et al. Comparison of glioma-associated antigen peptide-loaded versus autologous tumor lysate-loaded dendritic cell vaccination in malignant glioma patients. J Immunother. 2013;36(2): 152-7. doi.
Prins RM, et al. Gene Expression Profile Correlates with T-Cell Infiltration and Relative Survival in Glioblastoma Patients Vaccinated with Dendritic Cell Immunotherapy. Clinical cancer research 17.6(2011): 1603-1615.
Prins RM, et al. Immunology and immunotherapy in neurosurgical disease. Neurosurgery. 2003;53(1):144-53.
Prins RM, et al. Immunotherapeutic targeting of shared melanoma-associated antigens in a murine glioma model. Cancer Res. 2003;63(23):8487-91.
Pu K, et al. Bystander effect in suicide gene therapy using immortalized neural stem cells transduced with herpes simplex virus thymidine kinase gene on medulloblastoma regression. Brain Res. 2011; 1369:245-52.
Rauch, A., et al. (2008). Mutations in the Pericentrin (PCNT) Gene Cause Primordial Dwarfism. Science (80-.). 319.
Reinhart B, et al. Inhibition of Indoleamine-2,3-dioxygenase (IDO) in Glioblastoma Cells by Oncolytic Herpes Simplex Virus. Adv Virol. 2012;2012:815465. Epub Aug. 28, 2012. doi: 10.1155/2012/815465.
Retallack, H., et al. Zika virus cell tropism in the developing human brain and inhibition by azithromycin. Proceedings of the National Academy of Sciences 113.50 (2016): 14408-14413.
Rosenberg SA, et al. Adoptive cell transfer: a clinical path to effective cancer immunotherapy. Nature Reviews Cancer. 2008;8(4):299-308.
Rothlin, C. V, et al. TAM Receptors Are Pleiotropic Inhibitors of the Innate Immune Response. Cell 131.6 (2007)1124-1136.
Ryu CH, et al. Valproic acid enhances anti-tumor effect of mesenchymal stem cell mediated HSV-TK gene therapy inntracranial glioma. Biochem Biophys Res Commun. 2012;421(3):585-90. Epub Apr. 25, 2012. doi: 10.1016/j.bbrc.2012.04.050 PubMed PMID: 22525671.
Sampson JH, et al. An epidermal growth factor receptor variant III-targeted vaccine is safe and immunogenic in patients with glioblastoma multiforme. Mol Cancer Ther. 8. United States 2009. p. 2773-2779.
Sampson JH, et al. EGFRvIII mCAR-Modified T-Cell Therapy Cures Mice with Established Intracerebral Glioma and Generates Host Immunity against Tumor-Antigen Loss. 2014. doi: 10.1158/1078-0432.CCR-13-0709.
Sampson JH, et al. Greater chemotherapy-induced lymphopenia enhances tumor-specific immune responses that eliminate EGFRvIII-expressing tumor cells in patients with glioblastoma. 2011. doi: 10.1093/neuonc/noq157.
Sampson JH, et al. Immunologic Escape After Prolonged Progression—Free Survival With Epidermal Growth Factor Receptor Variant III Peptide Vaccination in Patients With Newly Diagnosed Glioblastoma. 2010. doi: 10.1200/JCO.2010.28.6963.
Sampson JH, et al. Intracerebral infusion of an EGFR-targeted toxin in recurrent malignant brain tumors. Neuro Oncol. 10. United States 2008. p. 320-329.

* cited by examiner

Figure 9

METHODS AND COMPOSITIONS FOR TREATING GLIOMA AND MEDULLOBLASTOMA BRAIN TUMORS USING THE ZIKA VIRUS

CROSS REFERENCE TO RELATED APPLICATIONS

This application is a continuation application of U.S. application Ser. No. 16/116,426, filed Aug. 29, 2018 which claims priority to U.S. Ser. No. 62/552,934, filed on Aug. 31, 2017, incorporated by reference herein.

GOVERNMENT GRANT INFORMATION

BACKGROUND

Brain Tumors

Primary tumors of the brain can arise from different types of cells in the central nervous system. Medulloblastomas are derived from precursors of neuronal cells while astrocytomas are derived from the astrocytic subset of glial cells, and oligodendrogliomas are derived from the oligodendroglia precursor subset of glial cells. Other types of primary tumors are derived from cells that form the inner and outer linings of the brain such as ependymomas from ependymal cells, and meningiomas from cells that comprise the meninges, respectively. Glioblastoma multiforme (GBM) derived from astrocytes is the most common and deadliest primary brain tumor and is therefore classified as astrocytoma WHO Grade IV. (1)

The current standard of care for GBM is an aggressive surgical resection followed by radiation treatments and chemotherapy. Even with advancements in intra-operative brain imaging, which have assisted with gross resections, new chemotherapies, and more focused radiation treatments, the prognosis for GBM remains extremely poor with survival rates of 33% for one year and a five year survival rate of 5%.(2) Advances in treating GBM have made great progress in recent years. Much of this progress is due to a greater understanding of the molecular subtypes of GBMs, the elucidation of glioma stem cells (GSC) and their role in self-renewal and resistance to therapy (3-5), and advances in biological therapies.

Molecular Classification of Glioblastoma Multiforme

In 2010 Verhaak et al. classified GBM into subtypes based on clinically relevant characteristics. These subtypes are classical, mesenchymal, proneural, and neural. (6) This information has furthered The Cancer Genome Atlas (TCGA) and may provide greater insight in future GBM treatment. Classical GBM is characterized by an increase amplification of epidermal growth factor receptor (EGFR), frequently has amplification of chromosome 7 and loss of chromosome 10. (6)

Patients with classical tumors benefit the most from a combination of temozolomide (TMZ) chemotherapy with radiotherapy. (7) Furthermore, the retinoblastoma protein (Rb) pathways are altered by CDKN2A deletion. (6) The mesenchymal group typically coincides with a decrease in neurofibromatosis 1 (NF1) expression and co-mutations of NF1, PTEN and AKT. (6) There is also an increase in necrosis and inflammation. (6) The proneural group is distinguished by alterations in PDGFRA and point mutations of IDH1.(6) Unlike the classical subgroup, the proneural subgroup has less prevalent amplification of chromosome 7 and loss of chromosome 10. (6) The proneural subgroup also displays the most CD133 expression, a GSC signature. Even though the proneural subgroup shows a high CD133 signature, the overall survival of these patients has been significantly higher. (7, 8) Finally, the neural subgroup exhibits expression of NF1, GABRA1, SYT1 and SLC12A5. (6) Verhaak et al also discuss how aggressive treatment is shown to be beneficial for classical and mesenchymal subgroups, effective for neural subgroup, and no change for the proneural subgroup. (6) One thought is the proneural subgroup does not respond to more aggressive treatment because of the amplification of CD133 which possesses cancer stem cell properties.(3)

The methylation of the MGMT promoter is another key prognostic factor in GBM. MGMT hyper methylation has been shown to be associated with increases in long term survival by 77.8%. (9) Additional studies by Noushmerher et al. identified glioma-CPG island methylation phenotype (G-CIMP) in glioblastoma and low-grade gliomas based on concentrated hypermethylation. Patients with G-CIMP tumors displayed IDH1 somatic mutations classifying them within the proneural subgroup. Furthermore, patients with G-CIMP were typically younger at the time of diagnosis and had an improved outcome which is consistent with the proneural subgroup classification. (6, 10)

An alternative method to classify brain tumors is according to the patient's age, tumor volume, and Karnofsky performance status (KPS). Zinn et al. evaluated patient outcomes according to those four categories. (8) Patients were given one point for presenting each of the following characteristics: over the age of 60, KPS of less than 100, or tumor volume greater than 30,000 $mm^3$. (8) Patients were then grouped according to their score, VAK-A for 0-1 points, VAK-B for 2-3 points. They concluded that VAK-A patients had a more favorable outcome considering they typically presented with greater p53 activation, longer median overall survival (20 months versus 12 months,) and displayed MGMT promoter methylation. (8)

Our ability to stratify GBM patients based on molecular biomarkers allows the identification of long-term vs. short-term survivors after treatment with current standard of care. Nevertheless, a 5% "long-term" survival rate for GBM patients 5 years after diagnosis is a poor prognosis. Biological therapies have now emerged, however, to provide possible curative approaches for treating malignant brain tumors.

Immunotherapy

Cancer immunotherapy is the stimulation of one's own immune system to activate specific immune cells to target and attack cancer cells. A major benefit of immunotherapy is its activation of immune surveillance against metastatic tumor behavior. (11) Additionally, it elicits adoptive immunity against cancer cells and memory T cells for recognition of recurrent tumor cells that exhibit previously expressed tumor antigens. The central nervous system (CNS), specifically the brain, was once considered immunoprivileged, however, studies have shown the brain is not a completely privileged site. Under normal conditions activated T-cells have been shown capable to cross the blood brain barrier (BBB) into the parenchyma. Nevertheless, studies also suggest that T-cells are required to be activated before they are capable of penetration, which is supported by studies showing that non-activated T-cells are limited on their ability to cross into the CNS. (12-14)

Furthermore, macrophages appear to be in abundance in CSF. (12) Radioactive antibodies have also been used to show a greater uptake of antibodies in conditions of brain cancers. This suggests that during a neuro-inflammatory disease state (e.g. encephalitis, meningitis, and cancer) antibodies and immune cells are more permeable to the BBB. (11) This gives rise to the potential use of immunotherapy against glioblastoma multiforme and other high grade gliomas. Immunotherapy methods currently used against high grade gliomas include, but not exclusive to the use of: activation and transfer of dendritic cells, adoptive T cell transfer, cytokines, and viral vaccines. (15)

Dendritic Cell Therapy

Dendritic cells (DCs) are so-called professional antigen presenting cells and are highly specialized in antigen processing, presentation, and playing a crucial role in adoptive immunity and immunological memory. (16) Even though DCs only represent a small fraction of circulating leukocytes, they play a major role in the immune surveillance. (17) DCs process and present antigens through the MHC I and II cell surface molecules and can activate both CD4+ and CD8+ T-cells. (16, 17) They can also assist in stimulating B-cells, and follicular DCs have also been shown to play a role in maintaining B cells memory. (16) DC vaccines use DCs loaded with antigens with the goal of initiating a T-cell antitumor response. (17)

After early animal models using DCs vaccinations demonstrated to be efficacious, safe, and capable of protecting mice re-challenged with tumors (18-20), the first pilot study using DC vaccination against brain cancer was performed at UCLA in 1997. (19-22) The first patient's time to progression following DC vaccination was 2 months with an overall survival of 21 months, displaying no significant adverse effects from the vaccine. (21) As a continuation of this pilot, Liau et al studied autologous tumor lysate (ATL) pulsed DCs in an intracranial rat model and demonstrated prolonged survival in the treatment group compared to the control, leading to a phase I trial; this phase I trial demonstrated efficacy in humans. (19, 23, 24)

In a more recent phase I clinical trial, Prins et al. examined the use of ATL-pulsed DCs versus glioma-associated antigen (GAA) pulsed DCs. (25) They concluded that the ATL treatment group had an increased median survival of 34.4 months compared to 14.5 in GAA. However, due to the high variance in the patient populations a meaningful comparison could not be made. (25) This study provides a look into the increased benefit of patient-specific therapy. Since then, many more DC clinical trials have been performed as shown below in Table 2, and there are approximately seven clinical trials currently active on Clinical Trails.gov. DC vaccines are shown to be safe with minimal adverse effects, with a benefit to overall survival, and allow for patient specific therapy making DC vaccination a compelling immunotherapy.

Vaccination With Tumor Specific Antigens

Epidermal Growth Factor Receptor variant III (EGFRvIII) is a tumor specific mutation commonly found in malignant gliomas. (26) The EGFR mutation encodes an active tyrosine kinase which leads to an increase tumorgenicity and migration, and patients exhibiting this mutation commonly results in poor prognosis. (26) This mutation however forms a tumor specific epitope which allows for immunotherapeutic targeting.(26, 27) In one of the first preclinical animal studies published using an EGFRvIII peptide conjugated with keyhole limpet hemocyanin, 70% of the treatment group displayed impalpable subcutaneous tumors, and in the intracranial tumor model the median survival increased by greater than 173% with 80% long term survivors. (28) This in vivo study showed the immune response was directed by NK and CD8+ T cells. (28) These early animal studies validated EGFRvIII vaccinations as a promising therapeutic and lead to multiple clinical studies.

Four clinical trials have been performed by using rindopepimut (CDX-110), an EGFRvIII specific peptide vaccine. (29) These clinical trials have shown both efficacy and the safety of this vaccine, leading to a current phase III trial in newly diagnosed GBM and a phase II in recurrent GBM. (29) An important EGFRvIII study was a multicenter phase II clinical trial using the EGFRvIII vaccine concurrently with TMZ, although TMZ induces lymphopenia, the EGFRvIII vaccine was able to induce an immune response eliminating EGFRvIII expressing tumor cells. (30) However, the phase III study, Act IV, was discontinued after interim analysis revealed no statistical benefit in overall survival. (31)

One difficulty with using EGFR inhibitors has been the development of tumor resistance. Sampson et al. found that of the twelve recurrent tumors analyzed after rindopepimut treatment, eleven had lost expression of EGFRvIII. (30) They suspect the loss of EGFRvIII expressing cells is due to the targeted therapy and clearance of these cells by the immune system. (30) However, Sequist et al. analyzed biopsies of 37 non-small cell lung cancer patients that had developed drug resistance to EGFR treatment.(32) Out of the 37 patients, 49% developed resistance through a T790 mutation, 14% from SCLC transformation, 5% from a MET amplification, 5% from a PIK3CA mutation, and finally 30% from an unknown mechanism. Understanding these tumor resistance mechanisms may give rise to using a combination of agents and better post resistance therapeutic treatments such as Engelman's combination of a MET inhibitor and EGF inhibitor.

Adoptive T Cell Transfer

Adoptive cell therapies are the largest division of immunotherapy for GBM and are continuing to grow. (33) Adoptive cell transfer (ACT) is a treatment which uses anti-tumor T-lymphocytes, autologous or allogeneic, expanded in vivo, then reinfused post lymphodepletion. (34) Currently the use of autologous tumor infiltrating lymphocytes is the most effective treatment for metastatic melanoma, resulting in 50% objectively responding and some patients exhibiting complete responses. (34) In an early clinical trial performed by Katakura et al 5 newly diagnosed GBM patients underwent ACT using yδT lymphonkine—activated killer (LAK) cells cultured in anti-CD3 mAb-coated flasks containing recombinant interlukin 2 (IL2)(35) This trial resulted in a median progression—free survival of 88 months, a median overall survival of 96.8 months, and no toxicity greater or equal to grade 2.(35) While this was a small clinical trial, this appears to be a promising approach in immunotherapy against GBM.

ACT has the capability of engineering T-lymphocytes to recognize a variety of antigens, making it useful for a variety of cancers. (34) The idea of engineering T-lymphocytes is a rapidly emerging area of research. One approach in which T-cells can be engineered is in the way they recognize antigens.

Two forms of antigen recognition being explored for ACT are T-cell receptors (TCRs) or chimeric antigen receptors (CARs). One of the major differences between CARs and TCRs is how they recognize their targets. (36) TCRs recognize antigens through major histocompatibility complex (MHC). Two restrictions of TCRs are autoimmunity from cross reactivity and the limitation by MHC complex formation on the number of potential targets.(37) On the other hand, CAR therapy is MHC independent and directly recognizes the target antigen.(36) CAR therapy is directed through antibody recognition and can be targeted towards any cell surface antigens. Some of the advantages of CAR therapy over TCRs are the number of antigens capable of targeting and high affinity targeting. (37) The higher affinity targeting of CAR therapy allows for less unforeseen autoimmune toxicity compared to TCRs. (37)

The outlook of CAR T-cells appears increasingly promising after Singh and Cooper (38) combined the novel Sleeping Beauty (SB) transposon/transponase system, developed by Hackett and colleagues (39), with T-cell engineering. Using SB to engineer CAR T-cells not only avoids using viral DNA, but has demonstrated to be faster and far less expensive compared to its viral recombination counterpart. (38, 40) In an ongoing phase I/II clinical trials, SB CD19 CAR T-cells have shown to be effective, resulting in all 4 patients with Non-Hodgkin's lymphoma remaining in remission after 3 months post infusion, and 1 acute lymphoblastic leukemia patient remaining in remission after 5 months. Additionally, there have been no acute or late toxicities to date. (41) Currently, there are three clinical trials activity recruiting patients to investigate SB CAR engineered T-cell usefulness in lymphoma and leukemia. In the context of brain cancer, there have been several preclinical studies using chimeric antigen receptors that have shown efficacy and currently an ongoing pilot study for autologous EGFRvIII CART cells (NCT 02209376).(42-51)

A second approach in which T-cells can be engineered are in the antigens they are specified to recognize. While T-cell engineering opens the door for targeting a large variety of antigens, emphasis should be place on choosing antigens not expressed by healthy tissue as autoimmune toxicity still remains as a major limitation to ACT. Likewise, the variability in response to ACT by patients makes it that much more difficult to predict unanticipated autoimmune adverse events.(36)

According to Hinrichs the four types of antigens that are ideal for targeting by ACT are those that are: expressed predominantly by germ cells, mutant gene products not expressed by healthy tissue, antigens restricted to nonvital tissue or cell lineages, or finally viral antigens.(36) Under these guidelines, some antigens that emerge as targets for gliomas include EGFRvIII, IL13Rα2, and human cytomegalovirus (HCMV). EGFRvIII is a suitable ACT target since it is a mutant gene not expressed by healthy tissue, and produces a novel peptide that is not normally found in the body. There have been several preclinical studies have been performed indicating the effectiveness of EGFRvIII CAR transduced T-cells.(47-49, 52) Miao et al. have displayed EGFRvIII CAR T-cell migration across the BBB and localization to the tumor region. (47) Moreover, Sampson and colleagues demonstrated that EGFRvIII CAR modified T-cells cured tumor bearing mice and generated anti-tumor immunity as evidenced by resisting tumor rechallenge with EGFRvIIINeg tumors. (49) These pre-clinical studies have demonstrated the feasibility and safety of EGFRvIII CAR mediated T-cells for clinical trials, which have already begun enrolling.(48)

Another glioma specific target for CAR T-cells is IL13Rα2. IL13Rα2 is a highly overexpressed cell surface receptor expressed in approximately 58% of adult gliomas. (46, 53) Thus far two clinical trials have been performed using IL13-zetakine CAR directed T-cells, which demonstrated feasibility without serious toxicity.(53) The overall survival and time to progression have not yet been published. However, one of the participants underwent a whole body and brain PET scan to detect localization of infused T-cells to the tumor regions.(54) It is anticipated that a second generation IL13Rα2 CAR T-cell clinical trial that will begin recruiting in the near future.

Human cytomegalovirus protein has been found in 90-100% of primary GBM making it an appealing target for ACT, but thus far only a handful of CMV-specific ACT clinical trials have been performed. (55) In a clinical trial using CMV-targeted T-cells, 10 of the patients recruited received a minimum of three infusions. Of these 10 patients 4 were progression free through the duration of the study. (56) The median overall survival was 403 days from the first recurrence, with minimal toxicity reported.(56) Additional clinical trials are needed to confirm efficacy and safety of CMV-specific ACT. One difficulty that has been noted for CMV immunotherapies has been overcoming the immunosuppressive tumor microenvironment.(55)

An alternative to targeting glioma specific antigens is targeting non-specific tumor associated antigens such as those prioritized by the National Cancer Institute for therapeutic targets and cancer vaccines. These antigens include: WT1, HER2, p53, MART1, gp100, the MAGEs and several more. (57)

The National Cancer Institute prioritization project ranked WT1 first amongst the other antigens used for therapeutic targets and cancer vaccines. (57) Wilms' tumor protein 1 (WT1) was previously described as a tumor suppressor gene, but is now shown to act as an oncogene. (58, 59) WT1 is a promising target because it is highly expressed in several solid tumors and hematological malignancies while only being expressed in a few normal tissues. Importantly, Driessche et al reviewed all reported WT-1 targeted immunotherapy cancer vaccine trials and found objective clinical responses in 46% of all solid tumors, and 64% in all hematological malignancies.(58) WT1 remains to be a safe therapeutic target, with only two patients having had severe adverse events, both patients had myelodysplasia syndrome.(58)

In contrast, MAGE-A3, a cancer testis gene, showed major cytotoxicity in a TCR-ACT clinical trial. Three of the nine patients treated with autologous anti-MAGE-A3 TCR engineered T-cells exhibited changes in mental status, two of which lapsed into comas and died. (60) Researchers suggest the initiating event was unrecognized MAGE-A12 expression in the brain. (60) Another common target of immunotherapies is human epidermal growth factor receptor 2 (HER2/ERBB2). HER2 is a growth receptor amplified in several cancers, including GBM, but is most commonly known for its amplification in breast cancer.(61) HER-2 has yet to be tested in a clinical trial against GBM, but several preclinical studies have been performed in medulloblastoma and GBM.(51, 62, 63) There have been no serious autoimmunity adverse events shown in the vaccine trials performed targeting HER2, yet cytotoxicity remains a concern due to the fact it is commonly expressed in vital tissue such as the heart, lungs, kidney, and bowels.(36) One method being explored to limit cytotoxicity from antigens expressed in healthy tissue is by engineering bispecific CAR T-cells. (64) In addition to limiting toxicity, bispecific CAR T-cells may provide a way to overcome recurrence from antigen null tumor cells that escape antigen targeting.(64) Using a binomial mathematical model, Hegde found dual targeting to be far superior to single antigen targeting in achieving near complete tumor cell capture. (64)

Gene Therapy

Gene therapy has been tested in numerous phase I clinical trials against brain tumors as well as pancreatic, lung, prostate, and renal carcinomas. While some forms of gene therapy have shown to be effective in certain cancers such as malignant melanoma and pancreatic cancer, few GBM clinical trials have advanced past phase II. (65) Like all other immunotherapy treatments, the goal of gene therapy is to provoke an immune response to destroy cancer cells. In a preclinical trial by Kuriyama et al HSV-tk-transduced murine hepatocellular carcinoma (HCC) cells were implanted subcutaneously into immunocompetent BALB/c mice and BALB/c nude mice. (66) Both groups were then treated with ganciclovir, however, only the immunocompetent mice displayed inhibition of tumor formation.(66) Furthermore, the immunocompetent mice exhibited infiltration by lymphocytes including CD4+ and CD8+. (66) This demonstrated that T-cell-mediated immune responses play critical role in HSV-tk gene therapy against cancer.(66) Many of the GBM trials have used either the adenoviral vector containing the herpes simplex virus thymidine kinase gene (AdV-tk), or herpes simplex thymidine kinase gene (HSV-tk) vectors as shown below in Table 3. These vectors have been used to deliver the p53 gene, a cell regulator and commonly causes apoptosis to cancer cells.(65) The combination of TK and granciclovir creates cytotoxic nucleotides selective for dividing cells and stops DNA synthesis. (67) The first measurable survival improvement trial was performed by Immonen et al using a combination of AdvHSV-tk and ganciclovir which resulted in median survival of 62.4 weeks in the treated group compared to 30.9 weeks in the control.(65, 67) While this study showed to be effective, many other clinical trials including a large phase III have not shown to be as effective. One of the problems with the HSV-tk retroviruses has been low penetration of brain tissue and low transduction efficiency.(67)

An alternative approach to inducing suicide gene therapy is using mesenchymal stem or neural stem cells expressing HSV-tk. Both mesenchymal stem and neural stem cell vehicles have been shown in preclinical studies to be safe and effective in achieving the bystander effect of suicide gene therapy. (68-72)

Cytokine gene vaccination is yet another form of gene therapy. Cytokine vaccinations consist of using cytokines or recombinant cytokines to elicit an anti-tumor response by the immune system. Unfortunately, many cytokines induce toxic reactions and are unstable in vivo. However, many delivery vehicles have been tested to overcome these adversities some of which include: adenoviral delivery, modified neural stem cells, or genetically engineered tumor cells. (19, 22, 73-75) The more commonly tested cytokines exhibiting efficacy against malignant gliomas are: granulocyte macrophage colony stimulating factor (GM-CSF,) Interferon alpha, and Interlukins IL-2, IL-4, and IL-12. Additionally, cytokine therapy can be used in combination with other immunotherapies such as DC, tumor lysate or tumor antigen vaccinations.(76-79) In one pre-clinical study GM-CSF with irradiated tumor cells increased the survival rate of intracranial tumor bearing rats compared to the control rats. (80) This study also showed combining IL-2 or IL-12 to the therapy lead to in an increased survival rate up to 90%.(80)

Oncolytic Viruses

Rather than using replication-incompetent viral vectors to deliver genes as discussed above with gene therapy, oncolytic virus therapy employ viruses with an active life cycle. Although both methods introduce viruses to kill cancer cells without harm to healthy cells, oncolytic viruses also use the patient's immune system to further attack the cancer cells enhancing the effectiveness of the treatment. (81) These tumor-selective viral replications results in lytic tumor cell destruction and subsequent release of thousands of vial progeny that go on to infect neighboring tumor cells. As a result, this method practices a local self-amplification therapeutic effect that is unique in comparison to all other forms of treatment.

There is significant concern in using replication competent lytic viruses in the brain which is heightened when considering the injection of pathogenic viruses. However, oncolytic viral therapy is particularly attractive to GBM patients because the tumor is confined to one organ and the tumor cells grow surrounded mostly by post-mitotic cells. Therefore, there is a reduced risk of the treatment damaging normal surrounding cells. Even so, only highly attenuated agents, or viruses that have substantial genetic modification deleting viral genes of harm, are typically considered. (81) Selective viral attenuation is typically considered to be vital to oncolytic viral therapy to create not only safer viruses but also increased tumor selectivity. A number of viruses have been modified and evaluated for their oncolytic potential. These include polio virus, herpes simplex virus, adenovirus, and measles virus.

Poliovirus

One of the most promising oncolytic viruses is the poliovirus. It has shown strong potential in its ability to target tumor cell killing and engage the host immune system. The potential of poliovirus stems from its unique mechanism of invading the host organism. The positive stranded RNA virus is a natural neuropathogen with neuroinvasiveness in particularly making it an ideal candidate for effective treatment against GBM. Early in the viral life-cycle, viral 2A protease is expressed and engages in rapid cleavage of key host cell components involved in mRNA export and translation. By disengaging the eukaryotic initiation factor (eIF) 4G and the nuclear pore complex, within 2-3 h the virus has shut down the host cell gene expression limiting antiviral responses that require biosynthesis. (82)

What is even more significant is that this does not affect the virus gene translation process. Simultaneously, in the absence of intact eIF4G viral replication and translation continues. Whereas usually, eIF4G is needed along with eIF4E to cap the 5'end of mRNA before undergoing translation, poliovirus uses a cis-acting genetic element in its 5' IRES to recruit ribosomal subunits. Therefore, its mechanism of attack overrides the host cell without engaging in complex parasitic relationships as most viruses do, allowing the virus to survive, replicate, and kill.

Its neuroinvasive quality stems from its ability to bind to the poliovirus receptor (PVR), commonly known as Necl-5 or CD155. These receptors are expressed on motor neurons. The binding of the two triggers receptor mediated endocytosis followed by a conformational change in the viral particle. (83) With this conformational change, a hydrophobic region becomes exposed on one of the capsid proteins enabling insertion into the endosomal membrane to form a pore where the viral genome can enter. Functional studies have since implicated Necl-5 involvement in cell invasion and intracerebral dispersion in glioblastomas. Furthermore, immunohisochemical studies have located the molecule in tumor cells at the invasive front of tumors. (84) Fluorescence-activated cell sorting and immunohistochemical studies of GBM patients' tumors confirmed universal and abundant expression of Necl-5. (85) Therefore, using poliovirus in oncolytic viral therapy may be the key to treating GBM.

In order to curtail the pathogenicity factor of the virus, the poliovirus IRES was genetically modified to be exchanged with a non-pathogenic version from human rhinovirus type 2 (HRV2). The chimera, RIPO, was then further modified to maximize attenuation. PVSRIPO was designed containing live attenuated SABIN poliovirus vaccine. Each vaccine contains a single point mutation in their respective IRES elements located in a distinctive stem loop domain, V, to prevent poliomyelitis. Overall, tumor specificity is then based on the affinity for the PVR that is upregulated in neruoectodermal malignancies and on functional growth deficit of the HRV2 IRES element in normal cells of neuronal derivation. (82) Together, with the attenuation SABIN vaccine strain, tumor specificity is achieved while highly reducing toxicity potential.

In previous work, exchanging the complete poliovirus IRES for the human rhinovirus type 2 (HRV2) IRES generated the chimera PV-RIPO that was shown to depresses viral translation and propagation in neuron-like cell lines (e.g., Sk-N-Mc and HEK-293).(86, 87) In addition, while the heterologous HRV2 IRES prevents virus propagation in spinal cord motor neurons without causing poliomyelitis, it has shown no effect on rapid viral growth in non-neuronal malignant cell types like those derived from malignant glioma cells.(88-90)

The genetic stability of the oncolytic non-pathogenic poliovirus recombinant was examined in vivo to be considered for therapy of recurrent glioblastoma multiforme. Bilateral HTB-15 xenografts were implanted in 12 athymic Balb/c mice to monitor tumor regression and enable virus recovery from the same animal. Ten days post inoculations, the median xenograft size had shrunk by 45%. (91) On day 20, the median xenograft size had shrunk by 45%.

Histopathology of xenografts from mice on day 20 (10 days post PVS-RIPO inoculation) showed identical responses in all 6 animals analyzed.(91) Advanced tumor cell lysis was observed with a bulk of the tumor no longer resembling the appearance of proliferating tumor. The majority of the tumor mass had vastly reduced cell content and was diffusely invaded by infiltrates. Because histopathology of xenografts 28 days post PVS-RIPO injection had essentially been replaced by a scar, it was assumed that the tissue rearrangement represented the host's reaction to tumor destruction leading to a transition towards scar formation. The histopathological analysis suggested that active PVS-RIPO replication in xenografts and a vigorous host response to the receding infected tumor induced complete tumor elimination resulting in scar formation.

Viral recovery has been analyzed in PVS-RIPO injected mice. Tumor lysates were first tested by plaque assay to confirm the presence of virus.(91) Xenografts from 6 animals 10 days post-inoculation were seen to contain infectious material while no infectious material was able to be recovered from tumors 28 days after inoculation of the virus. The latter was not surprising given the low amount of xenograft remaining at that interval, its histopathological appearance, and the very low vial titers in xenografts at 10 days post inoculation. Overall, these results suggest that PVS-RIPO is unable to persist in tumor once the supply of viable tumor cells has disappeared.

These in vivo xenograft experiments of tumor regression and virus recovery suggested a vigorous host response to viral tumor cell lysis evident by extensive infiltrative lesions within and surrounding the xenograft, perivascular cuffing, active tissue remodeling and, eventually, scarring. Furthermore, host inflammatory reaction contributes to virus removal once tumor obliteration eliminates the site of active viral replication. Together, PVS-RIPO is especially unique among oncolytic viruses for its safety and tumor-specific replication that partially relies on an abnormal environment for translation initiation in malignant glioma cells. These experiments support consideration of the agent to move to clinical trials against recurrent GBM.

Clinical trials of PVS-RIPO against recurrent glioblastoma brain tumors are ongoing at Duke University. A phase I trial (NCT01491893) was initiated to determine the maximally tolerated dose (MTD) or optimal dose of PVSRIPO when delivered intracerebrally by convection-enhanced delivery (CED) involving sterotactically placed catheters directly into the malignancy. Patients were infused with the virus over a span of 6.5 hours with a delivery rate of 0.5 ml/hr. Patients with Grade IV malignant glioma tumors were selected and subsequently analyzed post-injection for progression-free survival (PFS) and overall survival (OS). Results of the phase I study were reported at the 2014 American Society of Clinical Oncology meeting. At that time the phase 1 trial included 15 patients with recurrent supratentorial glioblastoma. The medial survival was 15.2 months and the 12-month survival rate was 70%. Furthermore, 18 and 24-month survival rates were 43.8% and 29.2%, respectively. In regards to safety, dose escalation through five levels eventually revealed dose-limiting toxicity at level 5. Adverse events considered potentially relevant to the study remained at or under grade 3. (92) Since this phase I report the FDA has granted PVSRIPO breakthrough status (93) thus accelerating its availability to other brain tumor centers across the country for treatment of patients with recurrent GBM.

Adenovirus

Adenovirus, a double-stranded non-enveloped DNA virus, is another oncolytic virus that has been widely studied for its potential in cancer treatment. In nature, the adenovirus is as a very common pathogen causing mild upper respiratory symptoms.(81) The adenovirus enters the cell by receptor mediated endocytosis. As the endosome matures and becomes more acidic, the virus goes through a process of un-coating steps to remove structural proteins from the capsid. (83) Some of these steps rely on a viral protease which becomes activated in the reducing environment of the endosome. One protein released from the capsid lyses the endosomal membrane, releasing the remainder of the virus into the cytosol. The virus then docks onto the nuclear pore complex and the DNA is transported into the nucleus to be transcribed.

In previous glioblastoma studies, the results for the traditional adenovirus serotype 5 (Ad5)-based vectors had disappointing results due to low expression of the adenovirus receptor (CAR) on GBM cells.(94) More recent modifications of the adenoviral vector system have been designed that combines the capsid of the wild-type Ad5 with fiber proteins of the adenovirus group serotype 35 (Ad35). This has shown to change the viral receptor from CAR to the human CD46 receptor which is up-regulated in tumor cells. (95) In addition, certain proteins from the E1A gene region in the adenovirus trigger cells to enter the S-phase in the cell cycle by interacting with cellular retinoblastoma tumor suppressor protein (pRb). Similarly, E1B proteins suppress apoptosis by binding and inactivating p53, thereby inhibiting its pro-apoptotic response. (96) Because of these interactions with vital tumor growth processes, these proteins are commonly targeted in treatment methodologies.

The adenovirus can be further modified to promote tumor-specific gene expression. By deleting all E1A and E1B genes within the adenovirus, the virus becomes replication incompetent in normal cells, cells without cell cycle dysfunction. This renders the adenovirus for oncolytic virus therapy tumor-selective. In one study, homologous recombination between inverted repeats (IR) in adenovirus genomes forms the basis of the design. Ad.IR vectors were modified to express tumor necrosis factor-related apoptosis-inducing ligand (TRAIL). (95) When the virus was evaluated, there was pronounced improvement in the effectiveness of targeting human glioblastoma cells through the CD46 receptor. Human glioblastoma cell lines U-87 MG, T98G, and SF767 all showed higher mean fluorescence with anti-CD46 antibody compared with an anti-CAR antibody, demonstrating the improved tumor-selectiveness of the adenovirus.

The oncolytic potential of Ad5/Ad35.IR-E1A/TRAIL has been evaluated in comparison to the traditionally studied adenoviruses (WTAd5, WTAd35, and Ad5/Ad35.IR-E1A/GFP). After virus infection, cells were observed for 6 days in vitro. For Ad5/Ad35.IR-E1A/TRAIL, all cell lines resulted in tumor cell death while little to no cell death was seen with the wildtype adenovirus. After injection of the wildtype adenovirus at the same dosage, cell death was still seen (less than 40%) but only in the SF67 cell line by WT-Ad35. U-87 and T98G cells showed no significant cell death after infection with WT-Ad5, Ad35, or Ad5/Ad35.IR-E1A/GFP. These results suggest the newly developed adenovirus system was more effective at inducing cell death attributing the finding to the apoptosis-inducing gene TRAIL key role.

Wohlfahrt et al (2007) also analyzed the comparison between Ad5.Ad35.IR-E1A/TRAIL and AD5.1R-E1A/TRAIL to assess the antitumor effect with the combination of Ad5 and Ad35 as a result of the receptor switch from CAR to CD46. Cells were infected with either Ad5.Ad35.IR-E1A/TRAIL or AD5.1R-E1A/TRAIL and apoptosis was observed using TUNEL assay. By the end of day 4, 20% to 30% more cells infected with Ad5.Ad35.IR-E1A/TRAIL underwent apoptosis for all cell lines. In contrast, no elevated levels of apoptosis were detected in wild-type Ad35 or Ad.5.IR-E1A/TRAIL. These results suggest that Ad5 combined with Ad35 was more effective at inducing apoptosis most likely due to altering the primary receptor of the virus.

Tumor growth was compared to the size of tumors in vivo with U-87 MG-untreated mice. Beginning 8 days post-injection, growth impairment was seen in tumor cells infected with Ad5.Ad35.IR-E1A/TRAIL with 40% less tumor volume than the negative control. The average growth remained reduced with about 40% to 50% volume reduction compared to the untreated tumors for the entire 20-day follow-up. While slight growth impairment was also seen in the Ad5, Ad35, and Ad5/Ad35.IR-E1/GFP-treated tumors, on average tumor size was only reduced by 20% to 40%. Altogether, only tumors treated with Ad5/Ad35.IR-E1/TRAIL showed a significant effect on inhibiting tumor growth. Ad5 (also known as ONYX-15) was tested in a phase I clinical trial for glioblastoma and showed no significant toxic side effects.(97) With these results, investigators are advancing the Ad5/Ad35.IR-E1/TRAIL protocol due to its improved infection and enhanced apoptosis outcomes that could quite possibly prove to be a more effective oncolytic virus therapy treatment in clinical trials.(95)

Measles Virus

The measles virus is a negative stranded, enveloped, RNA virus that also demonstrates viral oncolytic lysis potential to treat brain tumors. There are two measles virus glycoproteins, the hemagglutinin protein H and fusion protein F, that are imperative for oncolytic specificity and efficacy.(98-100) Hemagglutinin protein H binds to its receptor to initiate fusion. Mutated viral H protein displays a high affinity to CD46 receptors which is overexpressed on numerous tumor cells this key to the successfulness of oncolytic measles viruses. Next, fusion protein F simultaneously activates processes leading to syncytia formation and ultimately apoptosis.

Preclinical studies have investigated the therapeutic effectiveness of a highly attenuated measles virus known as the Edmonston stain (MV-Ed) that was designed to express carcinoembryonic agent (CEA). (101) MV-CEA was first evaluated In vitro to evaluate its ability to replicate and induce tumor cell death. Because the CD46 receptor is expressed abundantly on these tumors, glioma cell lines U251, U87, and U118 were preferentially studied. In all three cell lines, cell death was observed in over 90% of cells by 72 hours after being infected with MV-CEA. Less than 1% of cells were viable by 120 h after infection regardless of the cell line. Cell death was achievable with MV-CEA.

MV-CEA replication in glioma cells was determined after titers of the virus from the cells were obtained 24, 48, and 72 hours post infection. An increase in titer was associated with a significant rise in the CEA level which corresponds with viral replication/gene expression. CEA levels in uninfected glioma cells were undetectable. The mechanism of cell death was analyzed through TUNEL assays in all three glioma cell lines. Early after infection (day 2), syncytia was TUNEL-negative. By day 4, the nuclear clusters in 50% of syncytia showed TUNEL-positive nuclear staining and the cytoplasm was invariably negative. After day 6, there was positive diffuse staining throughout the cytoplasm, with residual positive nuclei and nuclear fragments, thus confirming apoptosis as mechanism of cell death.

In vivo studies evaluated the antitumor effect of MV-CEA using subcutaneous U87 glioma xenografts in BALB/c nude mice. (101) All mice treated with MV-CEA, exhibited complete regression of subcutaneous tumors as well as a significant prolongation of survival. Mice injected with 8×107 pfu MV-CEA had significant tumor regression as compared to mice treated with the same dose of UV-inactivated MV-CEA or untreated mice. The antitumor effect of MC-CEA was also evaluated in a mouse model that more closely resembles the disease in humans with intracranial U87 xenografts in BALB/c nude mice. Significant regression of the intracranial tumors after administering 3×105 pfu/dose for 6 doses, totaling a dose of 1.8×106 pfu, of MV-CEA. For these intracranial tumors, 7 out of 8 mice that received the MV-CEA treatment had complete regression of the tumor based on MRI. A phase I study to test the safety of the measles virus for patients with GBM is currently underway at the Mayo clinic (NCT00390299).

Herpes Simplex Virus

As one of the first oncolytic viruses to be adopted to attack cancer cells, Herpes Simplex Virus (HSV), it one of the most well understood viruses, easiest to manipulate, and relatively harmless in nature posing fewer risks and making it an ideal candidate virus. These factors propelled the advancement of HSV into oncolytic virus therapy. Entry into the cell requires the coordination between the 4 enveloped glycoproteins gB, gD, gH, and gL. Viral infection is initiated as gB and gC bind to surface proteoglycans. Next, gD interacts with the specific surface receptor prompting a conformational change in the glycoprotein. This leads to fusion of membranes by the activation of gB and the gH/gL heterodimer. In GBM patients, several strains of the virus including G207, HSV1716, and NV1020 have had success in clinical trials demonstrating antitumor potential without toxicity. Each mutant features deleted or manipulated viral genes to reduce toxicity without interfering with the infection of actively dividing cells. (102) Although there have been some promising patient responses (NCT00028158, NCT02031965), the overall effectiveness of herpes simplex viral vectors for oncolysis of GBM has been limited.

Taken together, greater specificity of targeting and efficacy by oncolytic viruses is needed for the treatment of brain tumors.

SUMMARY OF THE INVENTION

In one embodiment, the present invention is an anti-tumor composition comprising Zika virus, wherein the composition comprises a carrier suitable for direct intra-tumoral delivery. The composition additionally comprises a cancer vaccine, wherein the cancer vaccine is specific for glioblastoma multiforme (GBM) or medulloblastoma brain tumors.

In a preferred embodiment of the anti-tumor composition, the Zika virus and the vaccine are separate doses.

In another preferred embodiment, the vaccine comprises irradiated autologous GBM tumor cells previously infected with the Zika virus.

In another embodiment, the vaccine comprises irradiated allogeneic GBM tumor cells previously infected with the Zika virus. The vaccine may comprise irradiated allogenic tumor cells of the classical, mesenchymal, or proneural GBM phenotypes previously infected with the Zika virus.

In another preferred embodiment, the vaccine is administered with the cytokine GM-CSF.

In another preferred embodiment, the target tumor cells express the receptors AXL, DC-SIGN, TIM1, TYRO3, or any Zika-virus-associated receptor.

In another embodiment, the present invention is a method of treating GBM or medulloblastoma tumors, comprising the steps of (a) obtaining an anti-tumor composition comprising Zika virus, wherein the composition comprises carriers suitable for direct intra-tumoral delivery, (b) delivering the Zika virus composition to the tumor site, and (c) treating the patient with a tumor vaccine, wherein the tumor is treated.

In a preferred version of the invention, the delivery of the Zika virus is via injection.

In another version of the invention, the patient is treated with an initial dose of the composition. In another version, the patient with multiple doses of the tumor vaccine.

In one version of the invention, the tumor vaccine is specific for glioblastoma multiforme (GBM) or medulloblastoma brain tumors.

In one version of the invention, the tumor vaccine comprises irradiated autologous or allogenic GBM tumor cells or medulloblastoma tumor cells previously infected with the Zika virus.

In one version of the invention, the vaccine additionally comprises GM-CSF or IL-12.

In one version of the invention, the delivery of the virus into the intracranial tumor comprises delivering irradiated Zika virus or irradiated cells previously infected with the Zika virus.

DESCRIPTION OF THE DRAWINGS

Figure 9:
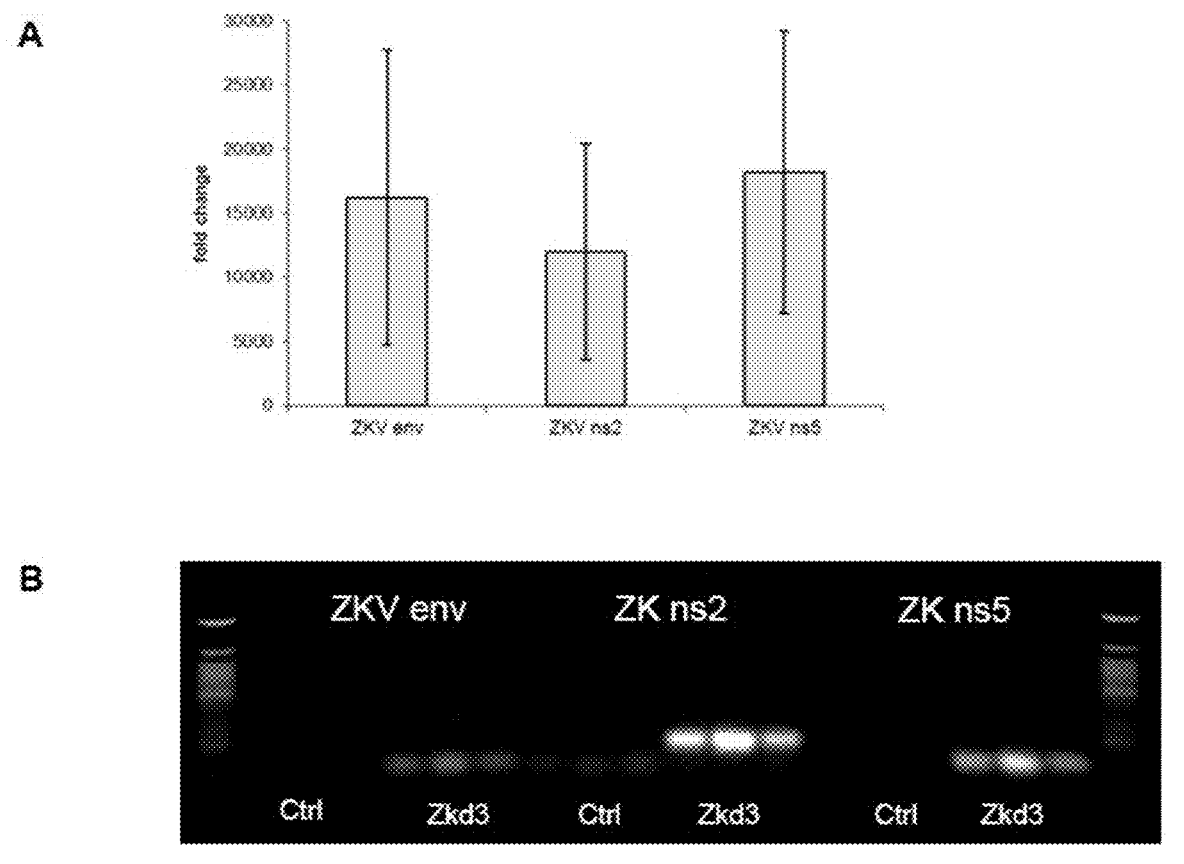

FIGS. 9 A and B demonstrates infection of human DAOY medulloblastoma cells by the Zika virus. A. To determine the ability of the Zika virus to infect human medulloblastoma cells, primers for qRT-PCR were used to target transcripts associated with the envelope of the Zika virus (ZKV env), and the ns2 and ns5 subunits of the virus for assessment of fold-change difference above controls. B. Gel electrophoresis was also conducted to determine relative abundance of transcripts to ZKV env, and the ns2 and ns5 subunits for human medulloblastoma cells cultured with the virus for 3 days (Zkd3) and compared with control (Ctrl) uninfected medulloblastoma cells.

DETAILED DESCRIPTION

Figure 1:
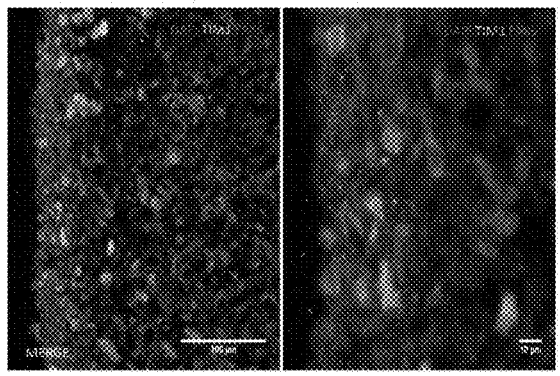
FIG. 1 discloses Zika virus TIM-1 receptors on neural progenitor cells. Left panel—low power image of human fetal cortex showing TIM-1 Zika virus receptor (green) and PAX6 neural marker (red). Right panel—high power image showing co-localization.

In general, the present invention includes methods and compositions for treating glioma and medulloblasoma brain tumors using the Zika virus. Embodiments of the invention and necessary background are discussed below.

Introduction (i) The Zika Virus

The Zika virus was first documented in the Zika Forest of Uganda in 1947 where it was found to infect non-human primates via mosquitos. This virus has recently emerged in South America and is transmitted to humans from bites by *Aedes aegypti* mosquitos. Transmission of the Zika virus from expecting mothers to their fetuses has resulted in devastating developmental abnormalities as seen by severe brain malformations (Soares de Oliveira-Szejnfeld, et al., 2016). Evidence suggests that the malformations of the developing brain are thought to be due to apoptosis of neural progenitor cells induced by Zika virus infection (Zhang et al., 2016).

Since the 2015 epidemic in Brazil, the number of cases of microcephaly has increased 20-fold in infants of ZIKV-infected mothers (Kleber de Oliveira et al., 2016). The association between infection and the diagnosis of Guillain-Barré Syndrome has also been noted (Oehler et al., 2014; Miller et al., 2017). Consequently, these episodes have prompted the World Health Organization to announce a Public Health Emergency of International Concern regarding ZIKV and its correlation with neurological disease (Heymann et al., 2016). Further interest has emerged as the virus has spread rapidly across the Americas by mosquitoes of the *Aedes* family (Dick et al., 1952). Still, much remains to be explored regarding ZIKV tropism within human cell types, and thus, motivated efforts are intended to expand our understanding of the virus' mechanisms of infection and how inhibition of the virus can be achieved. Currently, the long-term effects of the virus on infected individuals are unknown (Li et al., 2016).

ZIKV is a single-stranded, positive-sense RNA virus that codes for a single polyprotein. This protein is then later cleaved into three structural proteins (capsid, membrane, and envelope) and seven non-structural proteins (NS1, NS2A, NS2B, NS3, NS4A, NS4B, NS5) by host and viral proteases (Chakraborty, 2016; Lindenbach and Rice, 2003; Cunha et al., 2016). Although the information regarding ZIKV is relatively new, past studies analyzing the structure and pathogenesis of other closely-related flaviviruses have provided insight to the ZIKV life cycle. For example, it is known that in the early stages of infection, flaviviruses can protect infected cells from death for purposes of furthering viral replication (Gabriel et al., 2017). Additionally, comparisons between epitranscriptomes reveal that among known flaviviruses, N7 and 2'-O ribose methylations in the cap structure, initiated by the NS5 protein, are essential for capping and efficient replication of the virus (Stephen et al. 2016).

The cause of primary microcephaly is thought to be due to a depletion of radial glial cells (neural stem cells (NSCs) of the developing human brain) (Barkovich et al., 2012). Diversity in neuronal and glial cell types (neurons, astrocytes, oligodendrocytes) can be attributed to environmentally-determined NSC differentiation (Retallack et al., 2016). Therefore, it is unsurprising that we should find ZIKV preferentially targeting radial glial cells as well as their derivatives. Observed abnormalities in these infected cells such as centrosome perturbation, DNA reorganization, and other indications of mitotic alteration are thought to contribute to microcephaly in the developing brain (Souza et al., 2016).

Studies focused on NSCs in the adult brain have presented similar findings. After birth, these cell types are localized in the anterior subventricular zone of the forebrain and the subgranular zone of the hippocampal dentate gyrus in mice. Similar to NSCs in the developing brain, adult NSCs differentiate in response to environmental cues; they first give rise to intermediate progenitor cells (NPCs) and migrate to neurological niches that possess high vascular density, closeness to cerebrospinal fluid (CSF), and proximity to circulating viruses. It is here that the cells would differentiate and integrate into neuronal circuitry. However, viral infection instead leads to significant decreases in proliferation (Li et al., 2016).

(ii) Viral Entry

Host cell characteristics greatly influence the cell's susceptibility to viral infection. One of the characteristics of NSCs paramount to ZIKV infection is the TYRO3-AXL-MERTK (TAM) primary receptors (Rothlin et al., 2007). In addition to these features, DC-SIGN, TIM-1, and TIM-4 candidate attachment factors have also been suspected of promoting cell susceptibility to viral infection; however, gene expression analysis has displayed limited expression of DC-SIGN, TIM-1, and TIM-4 in radial glial cells of the developing human brain (Nowakowski et al., 2016; Wells et al., 2016). Similarly, it has been found that genes coding for DC-SIGN and TIM-1 are also low in expression in induced pluripotent stem cell (iPSC)-derived NPC's, suggesting that in these cell types, these particular receptors' involvement in cell entry mechanisms may be absent or of little prominence (Wells et al., 2016).

Comparatively, gene expression levels of TAM receptors are significantly higher, and they are therefore deemed more promising (Nowakowski et al., 2016; Wells et al., 2016). More specifically, AXL receptor has displayed mounting evidence prompting its characterization as a mediator to ZIKV entry. In order to test for viral infection in cells devoid of the AXL receptor, clustered regularly interspaced short palindromic repeats (CRISPR) and CRISPR associated protein 9 (Cas9) was used to knockdown AXL expression in ZIKV-infected human microglial cells. Interestingly, viral RNA internalized by host cells was significantly reduced (Meertens et al., 2017). Thus, this data further supports the involvement of AXL in viral entry mechanisms to host cells.

The expression levels of AXL have been explored in both in vitro and in vivo models. It has been found that AXL receptor genes are enriched in astrocytes, radial glial, endothelial, and microglial cell types of the developing human cortex, and they are similarly present in human iPSC-derived cerebral organoids (Nowakowski et al., 2016; Meertens et al., 2017). As it is known that U87 glioblastoma cell lines express high levels of astrocyte marker genes, CRISPR interference (CRISPRi) was used to knock down AXL expression after preceding ZIKV infection. The substantial decrease in infection supported hypotheses emphasizing AXL significance in viral entry (Retallack et al., 2016). It has also been found that during mid-neurogenesis, strong AXL expression is observable in the ventricular and subventricular zone of the developing human brain (Meertens et al., 2017).

Dengue Virus (DENV), another flavivirus closely related to ZIKV, also proceeds with viral infection by exploiting the AXL receptor. The virus undergoes viral apoptotic mimicry and binds indirectly to AXL via ligand growth arrest-specific gene 6 (Gas6). Gas6 recognizes and binds to phosphatidylserine, which is presented on the viral envelope surface. This bridge allows for the passage of virions to the receptor (FIG. 1). Receptor exposure to ZIKV enables the activation of AXL kinase activity and the passage of viral particles to the host cell via clathrin-mediated endocytosis (Meertens et al., 2017; Kim et al., 2017). Activation of AXL also downmodulates interferon signaling and contributes to enhanced infection of host cells by DENV. By investigating the importance of Gas6 on AXL-mediated infection by ZIKV virus, results have been found to be consistent with the mechanisms utilized by DENV. Human microglial cell lines (CHME3) exposed to ZIKV without the presence of TAM ligands also exhibited reduced infection among cells. To further validate these findings, CRISPR-Cas9 was performed to create AXL knockouts of CHME3 cells. Again, the internalized viral RNA was significantly reduced as compared to wild type cells. Upon internalization of viral particles, the viral envelope must undergo clathrin and dynamin-dependent endocytosis and deliver the particles to early endosomes. There, the mildly acidic environment triggers an irreversible conformational change in the viral envelope, promoting fusion of viral and host cell membrane (Meertens et al., 2017; Modis et al., 2004).

Despite evidence suggestive of AXL involvement, more recent findings propose AXL receptor may not be the sole component responsible for viral entry. After utilizing CRISPR/Cas9 deletion to excise the genes responsible for AXL expression, knockout hiPSC-derived NSCs and 3D cerebral organoids (derived from iPSCs) continued to display prevalent infection. Furthermore, a correlation between apoptotic marker cleaved caspase-3 (CASP3) and the viral envelope protein was found to exist within cerebral organoids, indicative of apoptosis of NSCs in vitro. Based on these findings, we can deduce that reliance on AXL alone for ZIKV host cell entry is insufficient, and the involvement of additional entry proteins characteristic of the host cell may be utilized in the facilitation of infection (Wells et al., 2016).

As it was hypothesized that receptor TYRO3 may be an additional factor contributing to ZIKV infection, this TAM receptor was also investigated as it is known to be co-expressed with AXL in differentiating NPCs. However, significant changes in TYRO3 gene expression remained absent after genetic ablation of AXL, indicating the receptor was not used as a compensatory mechanism (Wells et al., 2016). With these findings regarding TAM receptors, it is theorized that inhibition of both receptors may be necessary to achieve complete protection against ZIKV. Involvement regarding DC-SIGN and TIM-1 receptors may also contribute to mediating viral entry, and therefore the influence of additional receptors warrants further investigation.

(iii) Transcriptional Changes Following Infection

As a member of the TAM family, AXL is responsible not only for viral entry, but also for playing a unique role in clearing apoptotic cells and regulating neural stem cell immunity (Rothlin et al., 2007). It is known that when DENV-Gas6 complex activates AXL kinase activity, signaling through AXL contributes to the suppression of host cell innate immunity by inhibiting Interferon (IFN) I. Through IFN signaling, host cells gain the ability to suppress viruses by undergoing a potent antiviral state (Grant et al., 2016). Previous studies executed in murine models have also demonstrated that Gas6-coated viruses indeed activate AXL, dampen IFN I signaling, and promote infection in dendritic cells (Bhattacharyya et al., 2013; Meertens et al., 2012). To further explore the effects of AXL kinase activity on glial cell innate immunity, CHME wild type (WT) and AXL knockout cells were infected with ZIKV, and following infection, the mRNA of IFN-$\beta$, SOCS-1, and proinflammatory cytokine factors crucial to host cell immunologic response was quantified by qPCR. A significant increase in these factors was recognized in cells possessing AXL, providing additional evidence for AXL utilization for and enhancement of viral infection (Meertens et al., 2017).

At the conclusion of IFN signaling, STAT2, a signal transducer of transcription that lies downstream of the IFN I receptor, is phosphorylated and consequently activated. It is through initiation of STAT2 that upregulation of IFN antiviral genes results (Jabado et al., 2000). However, like DENV, expression of ZIKV nonstructural protein NS5 suppresses IFN I signaling. In 293T cells treated with IFN I, ZIKV NS5 was shown to strongly interact with STAT2. Consequent binding and degradation by the proteasome was later concluded, implying that activation of immunologic IFN-stimulated gene expression did not occur, and passage of ZIKV to host cells was made possible (Grant et al., 2016). Additional studies have displayed significance to the role of STAT2 in antiviral IFN signaling; infected STAT2 –/– murine models, it was discovered that infection of dendritic cells by ZIKV does not induce cytokine secretion by host cells. Again, the virus is not inhibited from further proliferation (Bowen et al., 2017).

In flaviviruses, the NS5 has been previously associated with mechanisms of replication and RNA synthesis; it encodes the RNA-dependent RNA polymerase and viral methyltransferase (MTase) domain (Grant et al., 2016). The N-terminal MTase domain is particularly involved in formation of the viral RNA cap (Coutard et al., 2017). However, mutations or defects of RNA methylation within the context of West Nile flaviviruses have proven detrimental and fatal to these pathogens; under normal conditions, precision and regulation of methylation are particularly important, and thus disturbances in methylation may contribute to perturbed homeostasis (Lichinchi et al., 2016). To further investigate the epitranscriptome of ZIKV, methylation of adenosine was pursued for its wide presence in eukaryotic mRNA and its probable role in pathological and physiological processes (Zheng et al., 2013; Frayling et al., 2007; Jia et al., 2011). It was found that as a result of ZIKV infection, methylation of adenosine location was altered, as well as the methylation motifs and target genes, suggesting that such alterations may influence CHME survival (Lichinchi et al., 2016).

(iv) Structural Changes and Induction of Host Cell Self-Consumption

The most significant factors affecting infected cell elimination are cell death and inhibited replication that could otherwise be used to compensate for cell loss. ZIKV inhibits brain development by infecting and attenuating growth and survival in fetal human NSCs; evidence supporting this hypothesis has been demonstrated through high apoptotic cell death and centrosome perturbation in cortical NSCs in monolayer culture, cerebral organoids, and neurospheres (Tang et al., 2016; Souza et al., 2016).

During NPC replication, perfect and unaltered centrosome function is crucial to rapid symmetric division, as disturbances can contribute to early differentiation. In cases of microcephaly of genetic origin, poor recruitment of centrosomal proteins results in incomplete spindle fiber formation as well as limited polarization of centrosomes in NSCs (Souza et al., 2016). As ZIKV infection of NPCs is already known to reduce recruitment of centrosomal proteins Cep152, PCNT, and CPAP, the lack of factors necessary for mitosis likely results in early differentiation for the NPC (Bond et al., 2005; Cizmeciog[l]u et al., 2010; Guernsey et al., 2010; Rauch et al., 2008). Supplemental evidence can be observed in infected in vitro NPC culture. Mitotic abnormalities following infection have included the development of micronuclei, supernumerary centrosomes, multipolar spindles, chromosome laggards, and the death of progeny after cell division (Souza et al., 2016). Fluorescent in situ hybridization was also performed on WT and ZIKV-infected NPCs; results displayed an increase in aneuploidy of chromosomes 12 and 17 in infected samples. This further contributes to incomplete host cell replication. Consequently, depletion in the NPC pool results (Gabriel et al., 2017).

Studies also suggest ZIKV may induce apoptosis of Sox2+ NPCs, as depletion of NPCs has been observed in iPSC-derived NPC cultures following infection. To detect and quantify apoptotic NPCs, CASP 3/7, 8, and 9 were used to identify and mark the transcription factor Sox2+, a feature prevalent and vital in the maintenance of stem cell properties throughout differentiation. DAPI staining displayed nuclear fragmentation, and flow cytometry analysis using annexin V and 7AAD staining also showed increased numbers of NPCs in early and late apoptosis in ZIKV-infected cultures when compared to mock-infected ones (Souza et al., 2016).

To assess the effects of viral infection on neurogenesis of NPCs in the adult brain of TKO mice, thymidine analog EdU and cell-cycle markers Ki67 and phospho-Histone H3 were used to label proliferating cells. Results were consistent with those found it NSCs of the developing brain; as compared to mock-infected mice, the number of proliferating cells was reduced in the SGZ and SVZ of infected mice. Staining for CASP3 was executed in wild type and ZIKV-infected TKO mice NPC populations, and colocalization between ZIKV and apoptotic presence suggests that ZIKV may induce apoptosis in NPCs in the SVZ and SGZ. These findings further indicate a decrease in NPC mitosis succeeding infection in the adult brain (Li et al., 2016).

The Present Invention (i) Methods of the Present Invention

In one embodiment, the present invention is a method of treating GBM or medulloblastoma tumors. In a preferred embodiment, the method comprises the steps of (a) obtaining an anti-tumor composition comprising Zika virus (as described below) and (b) delivering the Zika virus composition to the tumor site, wherein the tumor is treated.

In another embodiment, the present invention is a method of treating any tumor, wherein the target tumor cells express receptors for the Zika virus (e.g. the receptors AXL, DC-SIGN, TIM1, TYRO3, or any Zika-virus-associated receptor).

Preferably, the delivery method is via injection into the tumor mass. There are two preferable approaches. One could inject the Zika virus into the tumor cavity after resection of the tumor, such as described by E. A. Chiocca et al., (Molecular Therapy, 10:958-966, 2004) or inject the virus directly into the tumor after tumor recurrence, such as by using prior art methods similar to needle biopsies.

We envision that one embodiment of the invention would include a series of vaccinating inoculations would be done over a short period of time should be sufficient. However, if there is tumor recurrence at a later stage, for example due to a new gene mutation, then another series of inoculations using the newly mutated cells can be done.

Preferably, the dose of the Zika virus is in the range of $10^4$ to $10^8$ plaque forming units for intra-tumoral injections.

By "treatment" of the tumor, we mean any reduction in the growth rate or size of the tumor. Treatment may result in tumor shrinkage or disappearance. Treatment may also result in lack of further growth of the tumor or a reduction in growth rate.

Treatment success may be measured by an increase in the days of survival of the patient. Treatment success may also be measured by examining the target tumor and observing a decrease of mass size or a reduction or stabilization of tumor growth rate. Treatment success may also be measured by brain imaging using Mill technology.

Although lack of tumor growth and shrinkage would indicate a successful use of the present invention, the most preferred embodiment would be complete tumor regression, typically as revealed by brain imaging using MM.

In a preferred embodiment, the method additionally comprises the step of treating the patient with a tumor vaccine specific for glioblastoma multiforme (GBM) or medulloblastoma brain tumors, as described below. Preferably, the tumor vaccine comprises irradiated autologous or allogenic GBM tumor cells or medulloblastoma tumor cells previously infected with the Zika virus. Our results show that the combination of Zika virus injection and tumor vaccine enhances long-term survival.

In a preferred embodiment, the tumor vaccine cells have been frozen after irradiation and thawed before application.

The tumor vaccine is typically administered as described by the prior art. For example, the study by Liau et al., (J Immunotherapy, 36:152-157, 2014) used a cell vaccination of 1, 5, and 10×10⁶ dendrtic cells injected subdermally for their clinical study.

In another preferred embodiment of the invention, the tumor patient is additionally vaccinated with GM-CSF to attract antigen presenting dendritic cells. One may wish to substitute other useful cytokines, such as IL-12, for or in addition to GM-CSF.

Compositions of the Present Invention

In one embodiment, the present invention is an anti-tumor composition comprising Zika virus, wherein the composition comprises carriers suitable for direct intra-tumoral delivery. Preferably, the Zika virus is suspending in a carrier suitable for intra-tumoral delivery, such as a buffered solution designed to match the pH levels of the target tumor site.

In one version of the invention, the delivery of the virus into the intracranial tumor comprises delivering irradiated Zika virus or irradiated cells previously infected with the Zika virus.

By "Zika virus" we mean to include all strains, types, and sub-types of the Zika virus. A preferred strain is disclosed below in the Examples. Other preferred embodiments would use other wild-type, replication-competent strains. We also mean to include attenuated and modified forms of the Zika virus. For example, a viral form modified to prevent transmission or active infection might be preferred in certain applications. One would modify the Zika virus in ways analogous to other oncolytic viruses. For example, the article by Goetz and Gromeier (Cytokine & Growth Factor Reviews, 21:197-203, 2010) describes the attenuation of the poliovirus to target brain tumors. The authors used the attenuated Sabin virus, and replaced the IRES element in the virus genome with that from the human rhinovirus type 2. To develop an attenuated Zika virus, one could consider gutting the Zika virus to eliminate its ability to replicate.

In another embodiment, the anti-tumor composition additionally comprises a cancer vaccine, wherein the cancer vaccine is specific for glioblastoma multiforme (GBM) or medulloblastoma brain tumors. Typically, the anti-tumor composition and the vaccine are separate doses and administered separately. One would typically administer the doses on the same day, but the vaccination part could also be delayed if necessary. The vaccination part should typically be performed after the intra-tumoral injection of the Zika virus.

In one embodiment, the vaccine comprises irradiated autologous GBM tumor cells previously infected with the Zika virus. Preferably, the vaccine is administered along with the cytokine GM-CSF or a suitable substitute. One could look to prior art methods for preferable protocols. For example, Dranoff, Immunological Reviews, 1:147-154, 2002.

In another embodiment, the vaccine comprises irradiated allogeneic GBM tumor cells previously infected with the Zika virus. Preferably, the vaccine is administered with the cytokine GM-CSF. The allogenic tumor cells may be selected from classical GBM phenotype, mesenchymal GBM phenotype, proneural GBM phenotype, neural GBM phenotype or any combination of classical, mesenchymal, proneural, and neural GBM phenotype previously infected with the Zika virus.

In another embodiment, the anti-tumor composition comprises irradiated autologous or allogenic medulloblastoma tumor cells previously infected with the Zika virus.

The tumor vaccine cells are typically frozen after infection and then thawed prior to use.

EXAMPLES

The Zika Virus as an Oncolytic Virus and Vaccine Adjuvant

The Examples in the following section demonstrate that the human neural stem cells from the fetal brain express putative Zika virus receptors to which the virus can bind and enter the cells. The similarities between neural stem cells and brain tumor stem cells led us to postulate that the latter cells may also be susceptible to infection by the Zika virus. We provide examples on the infectivity of brain tumor cells by the Zika virus.

In spite of the dramatic malformations of the brain that occur in the developing human fetal brain that result from the infection of neural stem cells, adults who are infected by the Zika virus typically have a relatively benign course of illness with fever, rash, joint pain, and conjunctivitis (Duffy et al., 2009). A recent study, however, suggests that approximately 1% of adults infected with the Zika virus in South America experience some symptoms similar to Guillain-Barre Syndrome (Dos Santos et al., 2016). A case-control study of Zika virus infected adults with Guillain-Barre-like Syndrome in French Polynesia reported that clinical outcome of these patients were generally favorable with faster recovery compared to patients with typical Guillain-Barre Syndrome (Cao-Lormeau et al., 2016). These studies suggest that the Zika virus may not have long-term neurological consequences in adults and adolescents. These observations along with the propensity of the virus to infect brain tumor cells indicate that the Zika virus may be a suitable vector system to target brain tumor cells as an oncolytic virus and as a vaccine adjuvant to stimulate the immune system.

Figure 2:
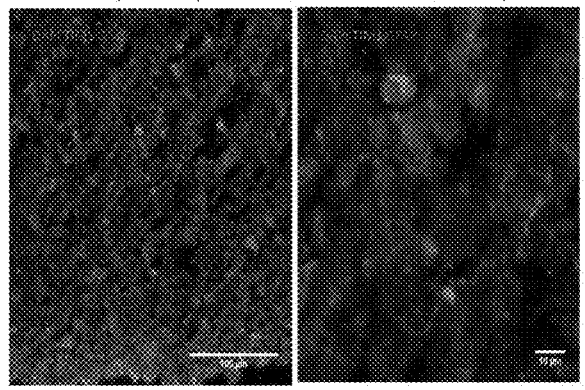
FIG. 2 discloses Zika virus TIM-1 receptors on fetal astrocytes. Left panel-low power image of human fetal cortex showing TIM-1 Zika virus receptor (green) and GFAP marker (red) for astrocytes. Right panel—high power image showing co-localization.

Hamel et al. (2015) recently reported that the Zika virus infects skin cells using DC-SIGN, TIM-1, AXL, and TYRO3 receptors. We have examined human fetal brain tissue by immunohistochemistry (IHC) and found the expression of these putative receptors on neural progenitor cells (FIG. 1) and on fetal astrocytes (FIG. 2).

Figure 3:
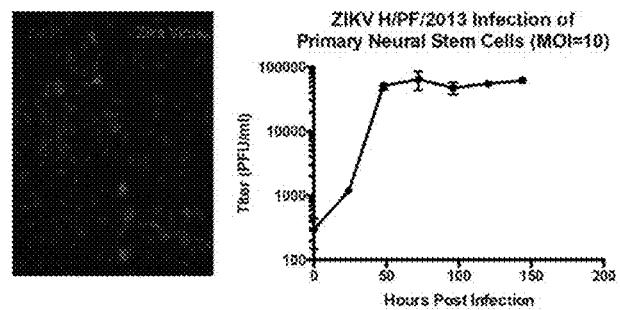
FIG. 3 shows Zika virus infection of neural stem cells. Left panel—Zika virus (red) and neural stem cells (blue). Right panel—Virus Infection rate.

To determine whether the Zika virus can infect human fetal neural stem cells, ZIKV H/PF/2013 (passage 4) was obtained from the European Virus Archive and propagated on Vero cells. Passage 6 virus used in our animal studies was concentrated and partially purified by ultracentrifugation over a 20% sucrose cushion. Incubation of the virus with human neural stem cells at an MOI of 10 resulted in a rapid infection that leveled off by 50 hours (FIG. 3).

Figure 4:
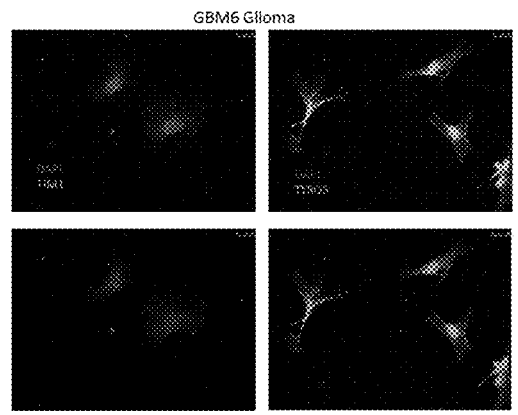
FIG. 4 shows expression of Zika virus receptors on human GBM6 glioma cells. Left panels—TIM-1 receptors (green). Right panels—TYRO3 receptors (green). DAPI to stain nuclei in upper panels (blue).

We previously demonstrated that brain tumor stem cells share similar properties with neural stem cells (REF Wu et al.) so we sought to determine whether brain tumor stem cells also express putative Zika virus receptors. We examined human GBM6 brain tumor cells by IHC and found that they also express DC-SIGN, TIM-1 (FIG. 4—Left panels), AXL, and TYRO3 (FIG. 4—right panels) receptors. Evaluation of the human U87 and murine GL261 glioma cell lines by IHC revealed a similar expression of these putative Zika virus receptors (data not shown).

Figure 5:
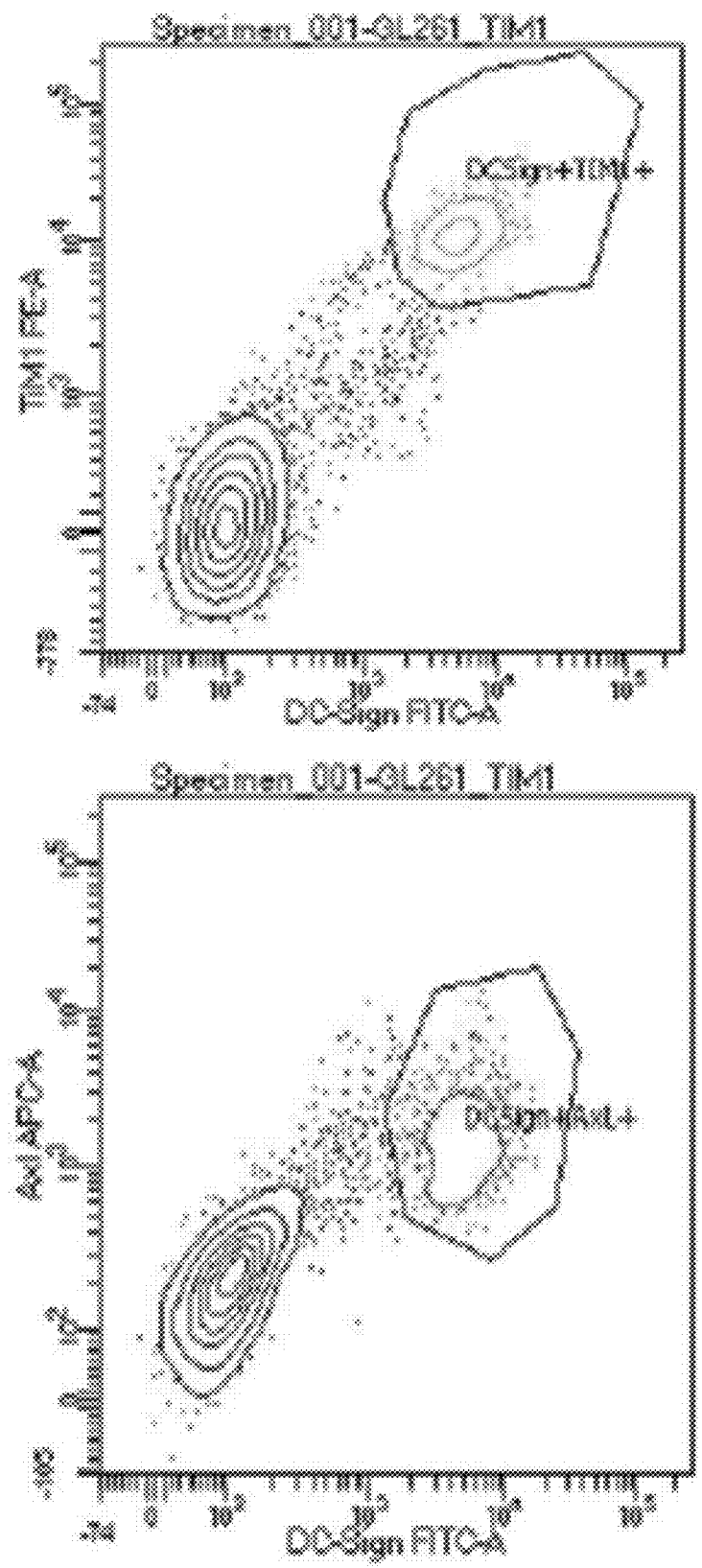
FIG. 5 demonstrates putative Zika virus receptors on murine GL261 glioma cells by flow cytometry. Upper Panel: Co-expression of DC-SIGN and TIM1 receptors (green). Lower panel: Co-expression of DC-SIGN and AXL receptors (pink).

Murine GL261 glioma cells were further studied by flow cytometry to determine co-expression of putative Zika virus receptors. We observed co-expression of DC-SIGN and TIM1; DC-SIGN and AXL for subpopulations of GL261 tumor cells (FIG. 5).

Figure 6:
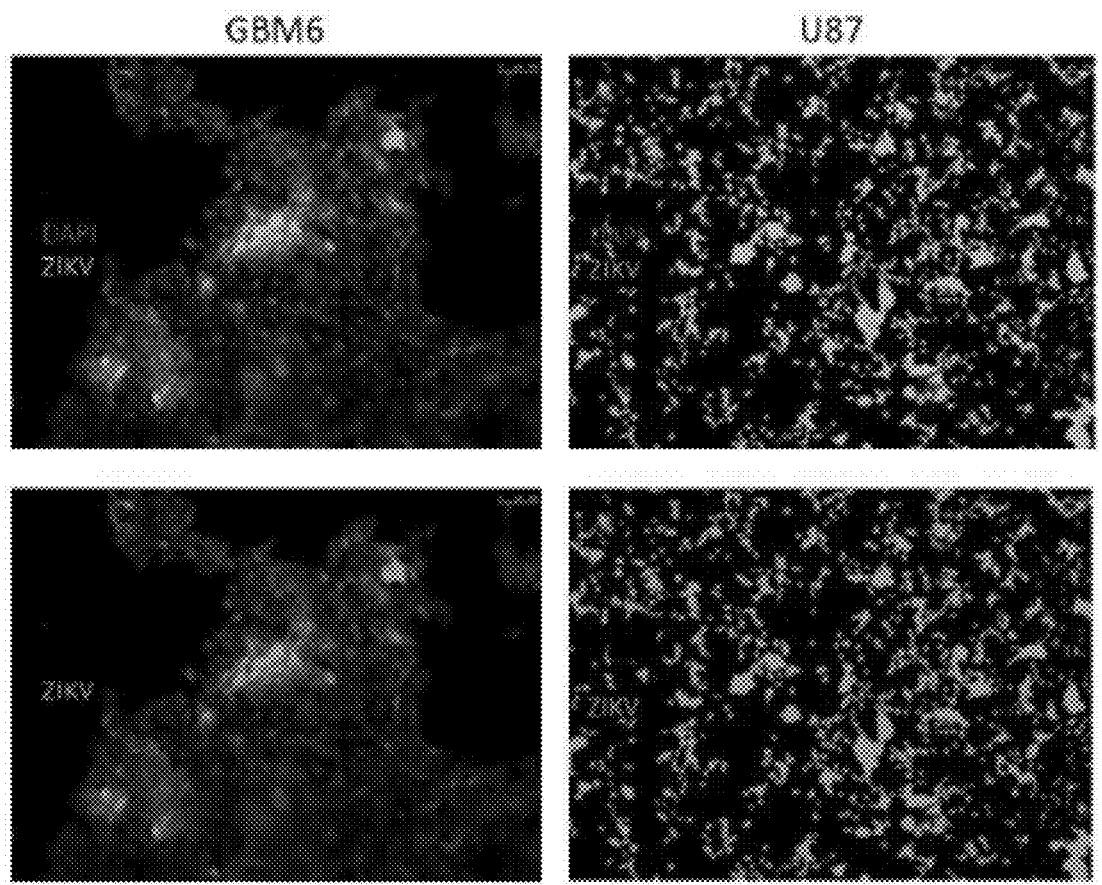
FIG. 6 shows Zika virus infection of human GBM cells. Left panels—GBM6 cells with Zika virus infection (green). Right panels—U87 GBM cells with Zika virus infection (green). DAPI staining for nuclei in upper panels (blue).

To determine the ability of the Zika virus to infect human brain tumor cells, the virus was incubated at an MOI of 10 with GBM6 or U87 tumor cells from 24 to 96 hours. We observed a high degree of infectivity (FIG. 6).

Figure 7:
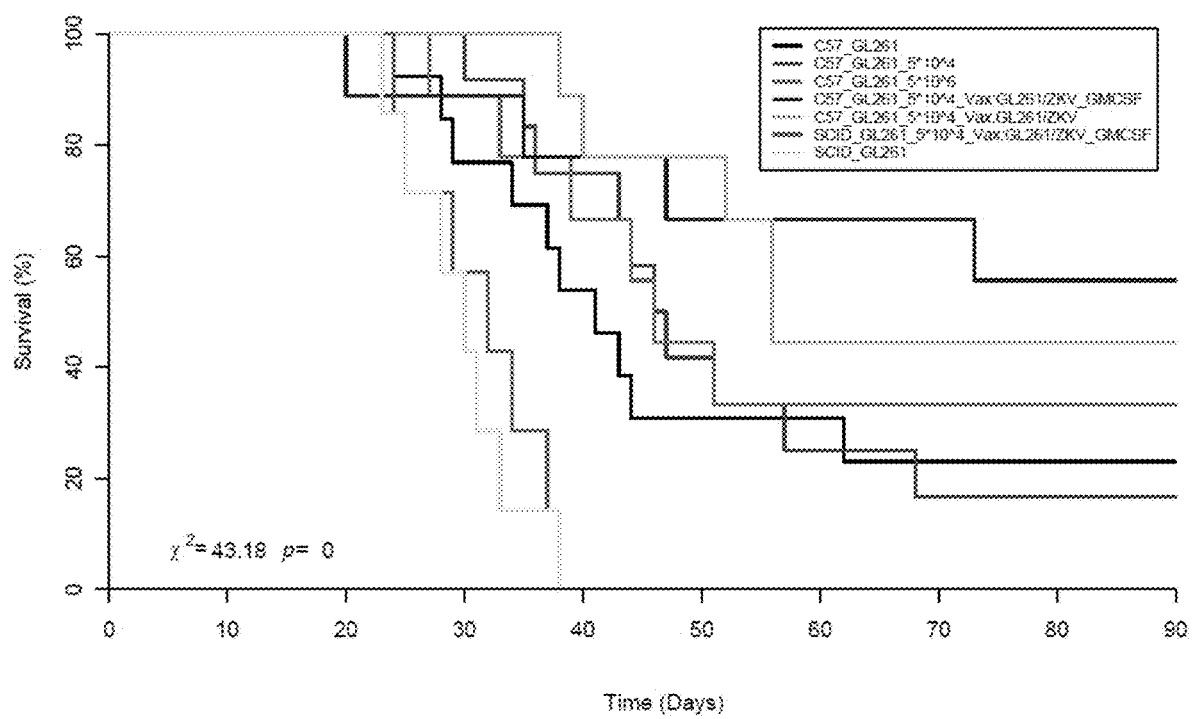
FIG. 7 is a set of graphs describing treatment and survival of C57B/6 mice with intracranial GL261 gliomas. Black—mice with GL261 tumors alone. Red—mice with tumors treated with intra-tumoral injection of Zika virus at a dose of $5 \times 10^4$. Green—mice with tumors treated with intra-tumoral injection of Zika virus at a dose of $5 \times 10^6$. Light blue—mice with tumors treated with intra-tumoral injections of the Zika virus followed by subcutaneous vaccination with irradiated tumor cells. Dark blue—mice with tumors treated with intra-tumoral injections of the Zika virus followed by vaccination and GM-CSF. Pink—immune deficient SCID mice with tumors treated with intra-tumoral injections of the Zika virus followed by vaccination and GM-CSR. Yellow—SCID mice with intracranial tumors and no treatment.
Figure 8:
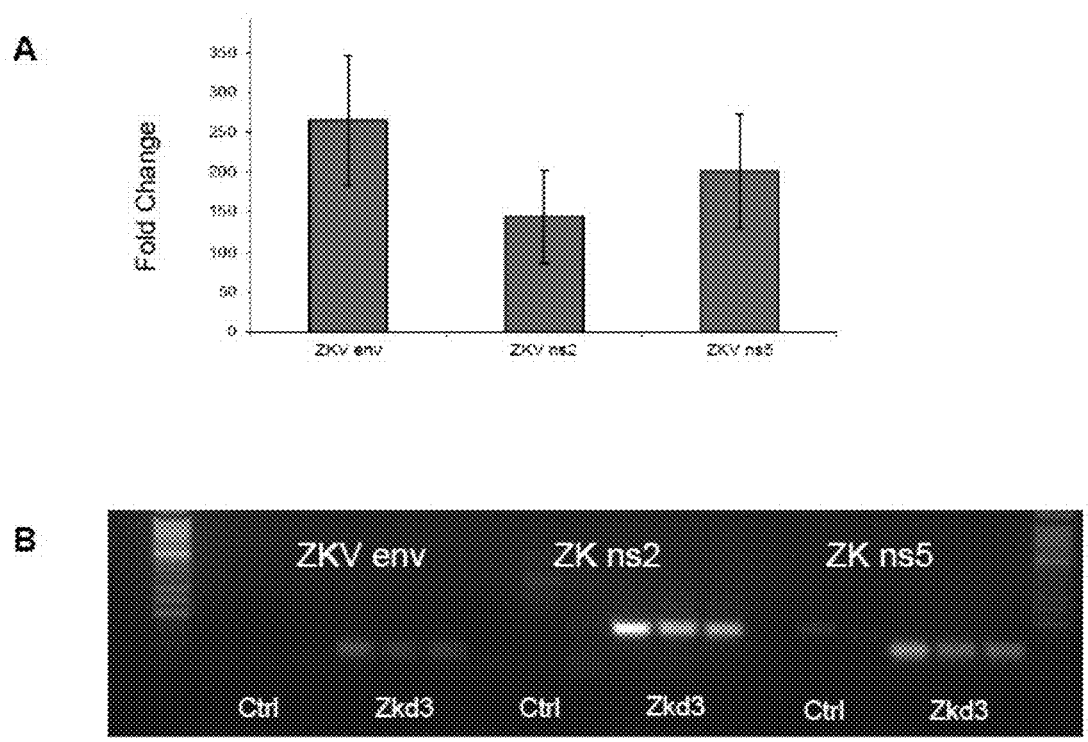
FIGS. 8 A and B demonstrates infection of human GBM6 malignant glioma cells by the Zika virus. A. To determine the ability of the Zika virus to infect malignant human gliomas, primers for qRT-PCR were used to target transcripts associated with the envelope of the Zika virus (ZKV env), and the ns2 and ns5 subunits of the virus for assessment of fold-change difference above controls. B. Gel electrophoresis was also conducted to determine relative abundance of transcripts to ZKV env, and the ns2 and ns5 subunits for human GBM6 cells cultured with the virus for 3 days (Zkd3) and compared with control (Ctrl) uninfected GBM6 cells.

We have studied the effects of using the Zika virus as an oncolytic virus and as a vaccine adjuvant. One group of C57B/6 mice were injected intracranially with 30,000 GL267 glioma cells. Their median survival time was 42 days (FIG. 7; black line group). A second group of mice with intracranial tumors were injected with the Zika virus into the tumor at a concentration of $5 \times 10^4$ viral particles. The median survival time for this group was 47 days (FIG. 7; red line group). A third group of mice with intracranial tumors were injected with the Zika virus into the tumor followed by peripheral subcutaneous vaccinations and days 3, 7, and 14 after tumor implantation. The vaccine consisted of $5 \times 10^6$ irradiated (60 Gy) GL261 tumor cells that were previously infected with the Zika virus for 4 days in culture. The median survival time for this group was 57 days (FIG. 7; light blue line group).

A fourth group of mice with intracranial tumors were treated with an intra-tumoral Zika virus injection, vaccination, and vaccination with GM-CSF to attract antigen presenting dendritic cells (DCs). The DCs process antigens for presentation and stimulation of antigen-specific CD8 and CD4 T cells. The median survival of this group was not determinable since over 50% of these animals continue to live long term (FIG. 7; dark blue line group). To demonstrate the critical role of CD8 and CD4 T cells in the vaccination group, athymic SCID mice that lack functional T cells received intracranial injections of tumor cells followed by vaccination and GM-CSF. This group had a median survival time of 32 days (FIG. 7; Pink line group). Taken together these results demonstrate that the combination of using the Zika virus as an oncolytic virus and vaccine adjuvant can significantly prolong survival in malignant brain tumors.

Examination of Second Species

Figure 10:
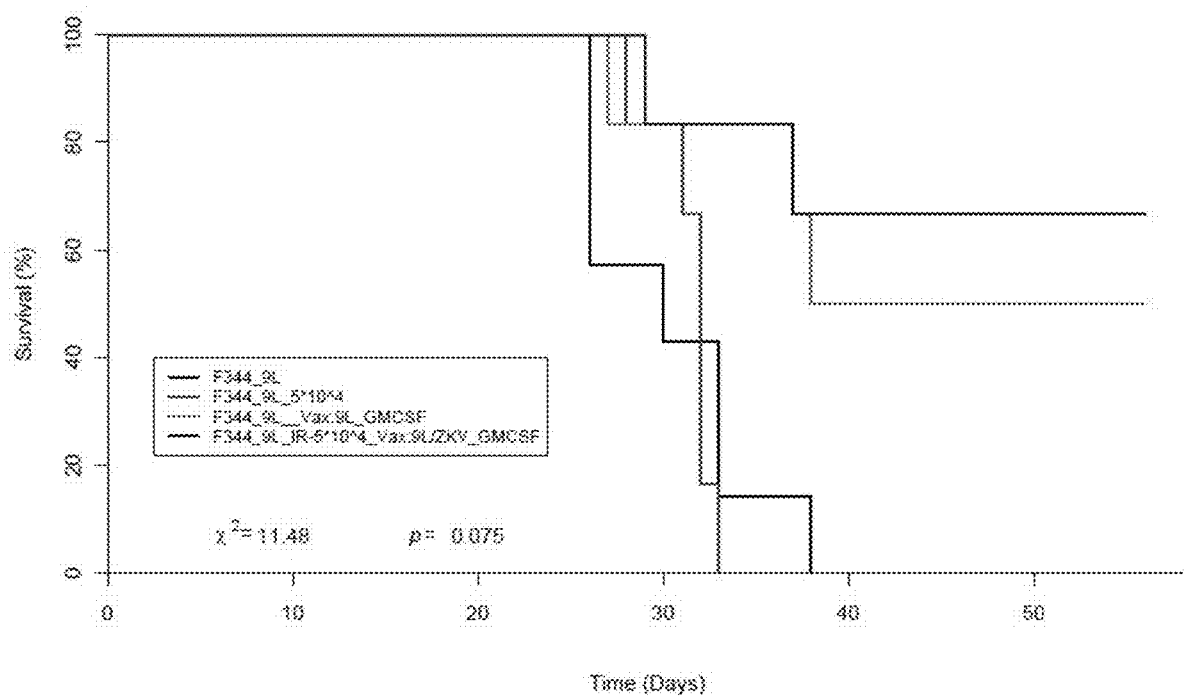
FIG. 10 graphs the treatment and survival of Fischer 344 rats with intracranial 9 L brain tumors. Black—rats with intracranial 9 L tumors and no treatment. Red—rats with intracranial 9 L tumors and intra-tumoral injections of Zika virus at a dose of $5 \times 10^4$. Green—rats with intracranial 9 L tumors and peripheral vaccination with irradiated 9 L tumor cells. Dark blue—rats with intracranial 9 L tumors and intra-tumoral injection of irradiated Zika virus and peripheral vaccination with irradiated 9 L tumor cells previously infected with Zika virus.

To determine the efficacy of Zika virus-based therapy on brain tumors in a second species, rats were evaluated with intracranial 9 L brain tumors. Rats with intracranial injection of 9 L tumor cells exhibited a median survival of approximately 32 days (black line, FIG. 10). Rats with intracranial 9 L tumors followed by intratumoral injections of the Zika virus at a dose of $5 \times 10^4$ viral particles exhibited a median survival of approximately 30 days (red line). Peripheral vaccination of rats with irradiated 9 L cells increased median survival to approximately 38 days (green line). In contrast, rats with intracranial 9 L tumors followed by intratumoral injection of irradiated Zika virus and peripheral vaccination irradiated 9 L cells also previously infected with the Zika virus exhibited approximately a 70% long-term survival rate (blue line).

To assess the long-term immunological consequences of Zika virus-based therapy C57BL/6 mice with GL261 intracranial brain tumors that exhibited long-term survival following peripheral vaccination with irradiated GL261 cells previously infected with the Zika virus were re-challenged with GL261 tumor cells intra-cranially implanted approximately 120 days after the initial tumor implantation and vaccination. This tumor-vaccine-tumor (T:V:T) re-challenge group was evaluated for the presence of immune cells by flow cytometry in the brain 7 days after the re-challenge. Control groups included long-term surviving C57BL/6 mice with GL261 tumors previously treated with Zika virus-based therapy and re-challenged with saline (T:V:S group); naïve C57BL/6 mice with de novo intracranial GL261 tumor implantation (N:T group); and naïve C57BL/6 mice with intracranial saline injection (N:S group).

Figure 11:
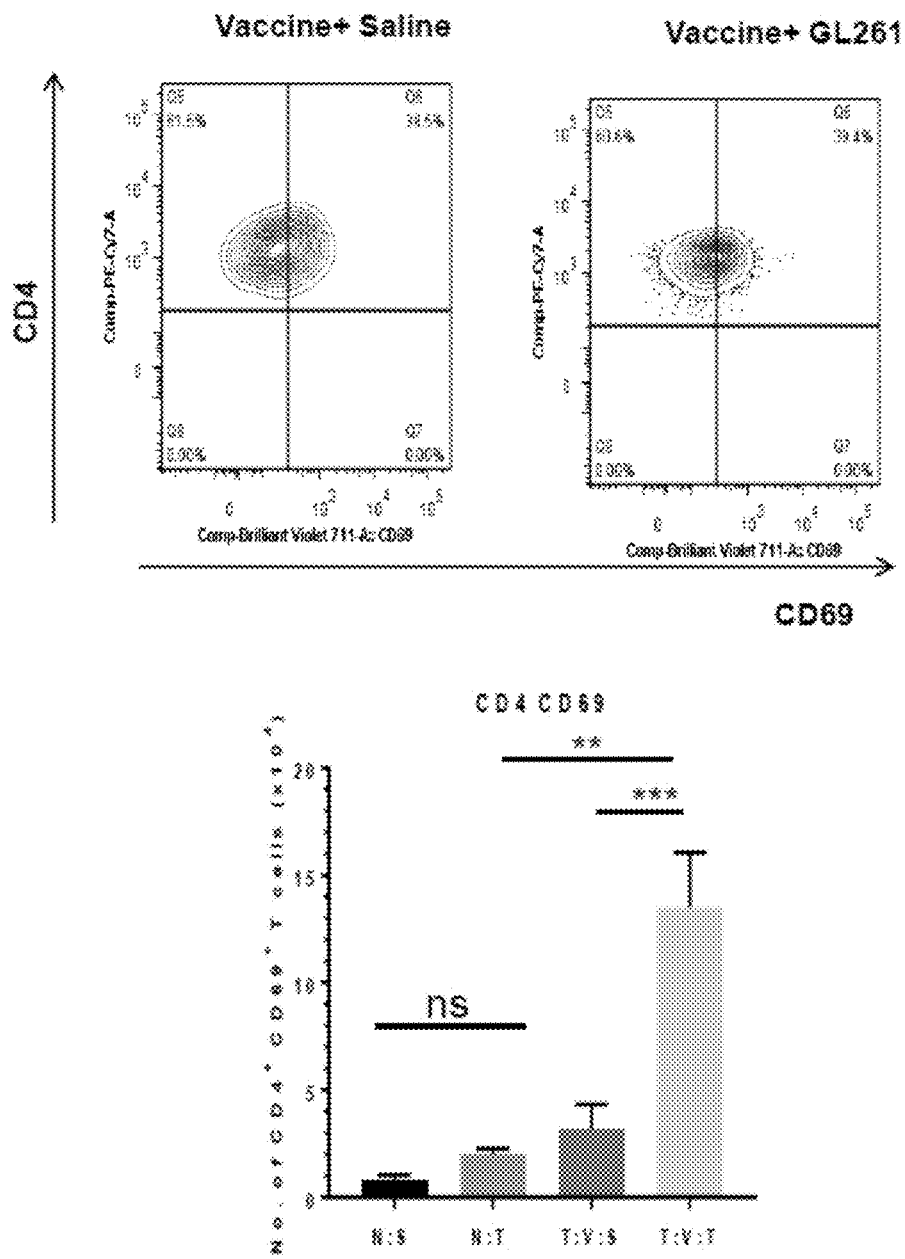
FIG. 11 graphs the long-term surviving C57BL/6 mice with previous GL261 brain tumors and then treated with Zika virus-based therapy exhibit increased activated CD4 T cells when re-challenged with intracranial GL261 tumors. Activated CD4 T cells identified by antibodies that recognize CD69 and CD4. Upper panel shows activated CD4 T cells in the brains of long-term surviving mice re-challenged with either a second brain tumor or saline. Lower panel shows the numbers (mean and standard error) of CD4$^+$/CD69$^+$ activated CD4 T cells in the brains of mice re-challenged with a second tumor (T:V:T group) or saline (T:V:S group). Data demonstrates that re-challenge with GL261 activates CD4 T cells in comparison to mice re-challenged with saline. Naïve mice with intracranial injection of saline (N:S group) or GL261 tumor (N:T group) exhibited no activation of CD4 T cells.
Figure 12:
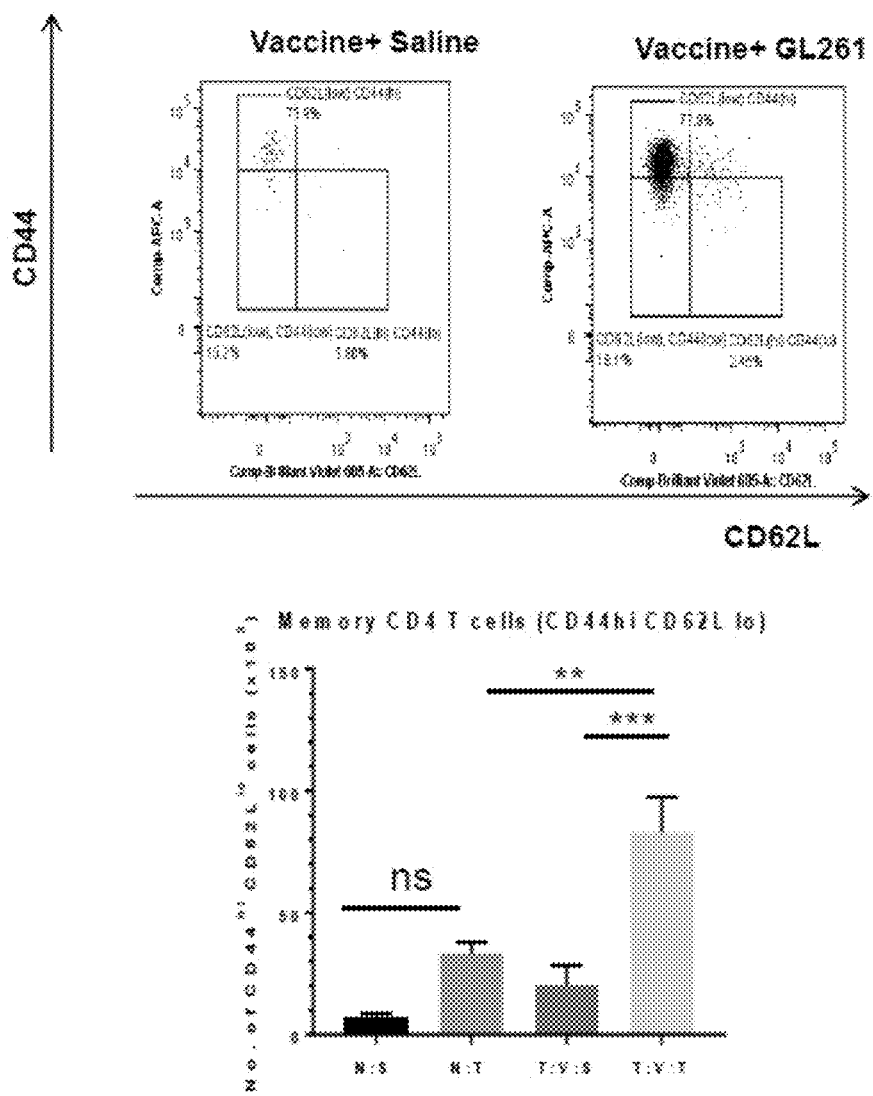
FIG. 12 shows long-term surviving C57BL/6 mice with previous GL261 brain tumors and then treated with Zika virus therapy exhibit increased memory CD4 T cells when re-challenged with intracranial GL261 tumors. Memory CD4 T cells identified by antibodies that recognize CD44$^{hi}$ and CD62L$^{lo}$. Upper panel show memory CD4 T cells in the brains of long-term surviving mice re-challenged with either a second brain tumor or saline. Lower panel shows the numbers (mean and standard error) of CD44$^{hi}$ and CD62L$^{lo}$ CD4 T cells in the brains of mice re-challenged with a second tumor (T:V:T group) or saline (T:V:S group). Data demonstrates that re-challenge with GL261 increases memory CD4 T cells in comparison to mice re-challenged with saline. Naïve mice with intracranial injection of saline (N:S group) or GL261 tumor (N:T group) exhibited no significant increase in the number of memory CD4 T cells.

CD4 T cells play a major role in the immune response against tumors. They can secrete cytokines that result in the destruction of tumor cells. Analysis if immune system response following intracranial GL261 tumor re-challenge resulted in a robust increase in activated CD4 T cells that also expressed CD69 in the T:V:T group in comparison to the T:V:S group that was challenged with saline, and the naïve groups (N:T and N:S) that were challenged with either tumor or saline, respectively (FIG. 11). In addition, analysis of memory CD4 T cells ($CD4^+/CD44^{hi}/CD62L^{lo}$) in the brain revealed that the long-term survivor group re-challenged with GL261 tumors (T:V:T group) exhibited a robust increase in memory CD4 T cells in comparison to the T:V:S, N:T, and N:S control groups (FIG. 12). Memory CD4 T cells are long-lived and quickly expand to large numbers of effector T cells when they encounter their cognate antigen. In this way they coordinate the immune system against previously encountered tumor antigens (Hwang M L et al., J Immunol, 179:5829-5838, 2007).

Figure 13:
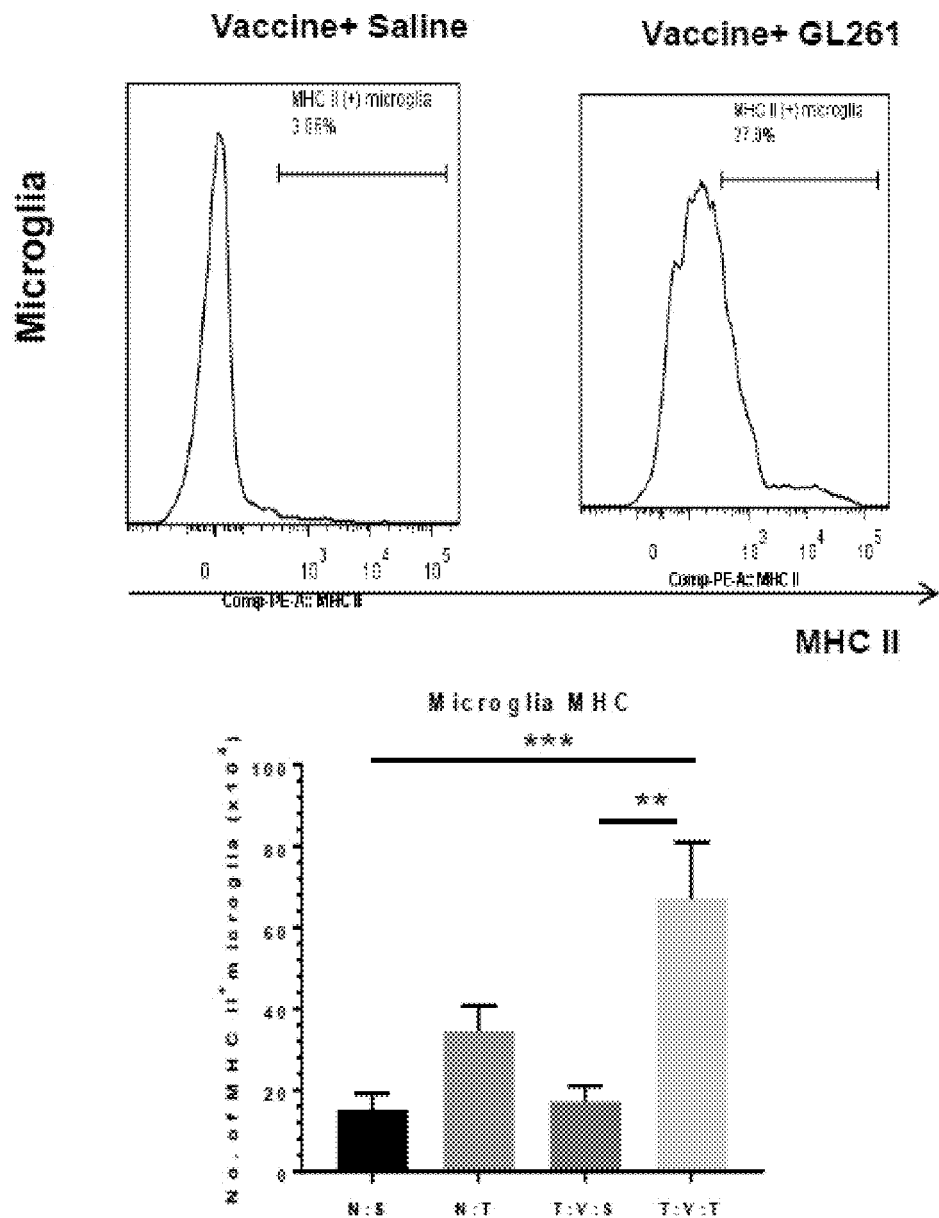
FIG. 13 shows long-term surviving C57BL/6 mice with previous GL261 brain tumors and then treated with Zika virus therapy exhibit increased MHC II$^+$ microglia cells when re-challenged with intracranial GL261 tumors. Microglia cells identified by antibodies that recognize CD45$^{int}$/CD11b$^+$/CD86/MHC II. Upper panel show Microglia MHC II cells in the brains of long-term surviving mice re-challenged with either a second brain tumor or saline. Lower panel shows the numbers (mean and standard error) of CD45$^{int}$/CD11b$^+$/CD86/MHC II microglia cells in the brains of mice re-challenged with a second tumor (T:V:T group) or saline (T:V:S group). Data demonstrates that re-challenge with GL261 increases microglia MHC II cells in comparison to mice re-challenged with saline. Naïve mice with intracranial injection of saline (N:S group) or GL261 tumor (N:T group) exhibited no significant increase in the number of microglia MHC II cells.

Microglia cells are phagocytic cells that process antigen for presentation using the cell surface molecule MHC II for stimulation of CD4 T cells. Within the immunosuppressive environment of brain tumors microglia expression of MHC II is down regulated (Tran C T et al., Neuropathology and Applied Neurobiology, 24:293-301, 1998). To determine the long-term effects of Zika virus-based therapy for brain tumors on microglia expression of MHC II the number of MHC II$^+$ microglia were quantified following tumor rechallenge. A robust increase in the number of microglia expressing MHC II was observed in T:V:T animals in comparison to the T:V:S, N:T, and NS control groups (FIG. 13). Together the CD4 T cell and microglia responses demonstrate that Zika virus-based therapy against brain tumors can engage long-lasting immune responses against tumor antigens.

REFERENCES

1. Central Nervous System Cancers NCCN.org: National Comprehensive Cancer Network; 2012 [cited 2012 Nov. 6, 2012]. Version 2.2012:[Available from: http://www.nccn.org/professionals/physician_gls/pdf/cns.pdf.
2. Wen P Y, Kesari S. Malignant Gliomas in Adults. The New England Journal of Medicine. 2008; 359(5):492-507. Epub Jul. 31, 2008. doi: 10.1056/NEJMra0708126.
3. Yan X, Ma L, Yi D, Yoon J-g, Diercks A, Foltz G, et al. A CD133-related gene expression signature identifies an aggressive glioblastoma subtype with excessive mutations. 2011. doi: 10.1073/pnas.1018696108.
4. Sgubin D, Wakimoto H, Kanai R, Rabkin S D, Martuza R L. Oncolytic herpes simplex virus counteracts the hypoxia-induced modulation of glioblastoma stem-like cells. Stem Cells Transl Med. 2012; 1(4):322-32. Epub Dec. 1, 2012. doi: 10.5966/sctm.2011-0035. PubMed PMID: 23197811; PubMed Central PMCID: PMCPmc3659700.
5. Wu A, Oh S, Wiesner S M, Ericson K, Chen L, Hall W A, et al. Persistence of CD133+ Cells in Human and Mouse Glioma Cell Lines: Detailed Characterization of GL261 Glioma Cells with Cancer Stem Cell-Like Properties. http://dxdoiorg/101089/scd20070133. 2008. doi: 10.1089/scd.2007.0133.
6. Verhaak R G W, Hoadley K A, Purdom E, Wang V, Qi Y, Wilkerson M D, et al. Integrated Genomic Analysis Identifies Clinically Relevant Subtypes of Glioblastoma Characterized by Abnormalities in PDGFRA, IDH1, EGFR, and NF1. doi: 10.1016/j.ccr.2009.12.020.
7. Le Mercier M, Hastir D, Moles Lopez X, De Neve N, Maris C, Trepant A L, et al. A simplified approach for the molecular classification of glioblastomas. PLoS One. 2012; 7(9):e45475. Epub Oct. 3, 2012. doi: 10.1371/journal.pone.0045475. PubMed PMID: 23029035; PubMed Central PMCID: PMCPmc3445522.
8. Zinn P O, Sathyan P, Mahajan B, Bruyere J, Hegi M, Majumder S, et al. A novel volume-age-KPS (VAK) glioblastoma classification identifies a prognostic cognate microRNA-gene signature. PLoS One. 2012;7(8):e41522. Epub Aug. 8, 2012. doi: 10.1371/journal.pone.0041522. PubMed PMID: 22870228; PubMed Central PMCID: PMCPmc3411674.
9. Etcheverry A, Aubry M, de Tayrac M, Vauleon E, Boniface R, Guenot F, et al. DNA methylation in glioblastoma: impact on gene expression and clinical outcome. BMC Genomics. 2010;11(1):701. doi: 10.1186/1471-2164-11-701.
10. Noushmehr H, Weisenberger D J, Diefes K, Phillips H S, Pujara K, Berman B P, et al. Identification of a CpG island methylator phenotype that defines a distinct subgroup of glioma. Cancer Cell. 2010; 17(5):510-22. Epub Apr. 20, 2010. doi: 10.1016/j.ccr.2010.03.017. PubMed PMID: 20399149; PubMed Central PMCID: PMCPmc2872684.
11. Ostrand-Rosenberg S. Immune surveillance: a balance between protumor and antitumor immunity. 2008; 18(1): 11-8. doi: 10.1016/j.gde.2007.12.007.
12. Choi B D, Duke Brain Tumor Immunotherapy Program DoN, Department of Surgery, Duke University Medical Center, Durham, N.C. 27710., Department of Pathology DUMC, Durham, N.C. 27710., Archer G E, Duke Brain Tumor Immunotherapy Program DoN, Department of Surgery, Duke University Medical Center, Durham, N.C. 27710., Department of Pathology DUMC, Durham, N.C. 27710., et al. EGFRvIII-Targeted Vaccination Therapy of Malignant Glioma. Brain Pathology.19(4):713-23. doi: 10.1111/j.1750-3639.2009.00318.x.
13. Lotan. M S M. Cross talk between the immune system and the nervous system in resonse to injury: implications for regeneration 2012. Available from: http://www.fasebj.org/content/8/13/1026.full.pdf.
14. Ni H T, Merica R R, Spellman S R, Wang J M, Low W C. Visualization of antigen-specific T cell activation in vivo in response to intracerebral administration of a xenopeptide. Exp Neurol. 164. United States: 2000 Academic Press.; 2000. p. 362-70.
15. Prins R M, LM L. Immunology and immunotherapy in neurosurgical disease. Neurosurgery. 2003; 53(1):144-53. doi: 10.1227/01.NEU.0000068865.34216.3A.
16. Wieder E. Dendritic Cells: A Basic Review: International Society of Cell Therapy; 2003 [cited Dec. 1, 2012]. Available from: http://www.celltherapysociety.org/files/PDF/Resources/OnLine_Dendritic_Education_Brochure.pdf.
17. MD Consult—Dendritic Cell Vaccines for Brain Tumors—Neurosurgery Clinics of North America—Medical Journal. 2010.
18. Ni H T, Spellman S R, Jean W C, Hall W A, Low W C. Immunization with dendritic cells pulsed with tumor extract increases survival of mice bearing intracranial gliomas. J Neurooncol. 2001; 51(1):1-9. Epub May 15, 2001. PubMed PMID: 11349874.
19. Liau L M, Black K L, Prins R M, Sykes S N, DiPatre P L, Cloughesy T F, et al. Treatment of intracranial gliomas with bone marrow-derived dendritic cells pulsed with tumor antigens. J Neurosurg. 1999; 90(6):1115-24. Epub Jun. 1, 1999. doi: 10.3171/jns.1999.90.6.1115. PubMed PMID: 10350260.
20. Heimberger A B, Crotty L E, Archer G E, McLendon R E, Friedman A, Dranoff G, et al. Bone marrow-derived dendritic cells pulsed with tumor homogenate induce immunity against syngeneic intracerebral glioma. Journal of Neuroimmunology. 2000; 103(1):16-25. PubMed PMID: 10674985.
21. Linda M. Liau, Keith L. Black, Neil A. Martin, Steven N. Sykes, Jeff M. Bronstein, Lisa Jouben-Steele, et al. Treatment of a glioblastoma patient by vaccination with autologous dendritic cells pulsed with allogeneic major histocompatibility complex class I-matched tumor peptides. http://dxdoiorg/103171/foc2000969. 2007. doi: FOC.2000.9.6.9.
22. Broder H, Medicine UoCaLASo, Anderson A, Medicine UoCaLASo, Kremen T J, Medicine UoCaLASo, et al. MART-1 adenovirus-transduced dendritic cell immunization in a murine model of metastatic central nervous system tumor. Journal of Neuro-Oncology. 2014; 64(1-2):21-30. doi: 10.1007/BF02700017.
23. Linda M. Liau, Keith L. Black, Robert M. Prins, Steven N. Sykes, Pier-Luigi DiPatre, Timothy F. Cloughesy, et al. Treatment of intracranial gliomas with bone marrow-derived dendritic cells pulsed with tumor antigens. http://dxdoiorg/103171/jns19999061115. 2009. doi: 10.3171/jns.1999.90.6.1115.
24. Liau L M, Prins R M, Kiertscher S M, Odesa S K, Kremen T J, Giovannone A J, et al. Dendritic Cell Vaccination in Glioblastoma Patients Induces Systemic and Intracranial T-cell Responses Modulated by the Local Central Nervous System Tumor Microenvironment. 2005. doi: 10.1158/1078-0432.CCR-05-0464.
25. Prins R M, Wang X, Soto H, Young E, Lisiero D N, Fong B, et al. Comparison of glioma-associated antigen peptide-loaded versus autologous tumor lysate-loaded dendritic cell vaccination in malignant glioma patients. J Immunother. 2013; 36(2):152-7. doi: 10.1097/CJI.0b013e3182811ae4. PubMed PMID: 23377664; PubMed Central PMCID: PMC3568250.
26. Sampson J H, Archer G E, Mitchell D A, Heimberger A B, Bigner D D. Tumor-specific immunotherapy targeting the EGFRvIII mutation in patients with malignant glioma. 2008; 20(5):267-75. doi: 10.1016/j.smim.2008.04.001.
27. Wu A H, Xiao J, Anker L, Hall W A, Gregerson D S, Cavenee W K, et al. Identification of EGFRvIII-derived CTL epitopes restricted by HLA A0201 for dendritic cell based immunotherapy of gliomas. J Neurooncol. 2006; 76(1):23-30. Epub Sep. 13, 2005. doi: 10.1007/s11060-005-3280-7. PubMed PMID: 16155724.
28. Heimberger A B, Crotty L E, Archer G E, Hess K R, Wikstrand C J, Friedman A H, et al. Epidermal Growth Factor Receptor VIII Peptide Vaccination Is Efficacious against Established Intracerebral Tumors. 2003.
29. Babu R A D. Rindopepimut: an evidence-based review of its therapeutic potential in. 2012. doi: 10.2147/CE.S29001.
30. Sampson J H, Aldape K D, Archer G E, Coan A, Desjardins A, Friedman A H, et al. Greater chemotherapy-induced lymphopenia enhances tumor-specific immune responses that eliminate EGFRvIII-expressing tumor cells in patients with glioblastoma. 2011. doi: 10.1093/neuonc/noq157.
31. Data Safety and Monitoring Board Recommends Celldex's Phase 3 Study of RINTEGA® (rindopepimut) in Newly Diagnosed Glioblastoma be Discontinued as it is Unlikely to Meet Primary Overall Survival Endpoint in Patients with Minimal Residual Disease (NASDAQ: CLDX) [Internet]. 2016. Available from: http://ir.celldex.com/releasedetail.cfm?ReleaseID=959021

32. Sequist L V, Waltman B A, Dias-Santagata D, Digumarthy S, Turke A B, Fidias P, et al. Genotypic and Histological Evolution of Lung Cancers Acquiring Resistance to EGFR Inhibitors. 2011. doi: 10.1126/scitranslmed.3002003.

33. Bielamowicz K J, kevinbvich@yahoo.com, Khawja S, khawja@bcm.edu, Ahmed N, nmahmed@bcm.edu. Adoptive Cell Therapies for Glioblastoma. Cancer Genetics. 2013; 3. doi: 10.3389/fonc.2013.00275.

34. Rosenberg S A, Restifo N P, Yang J C, Morgan R A, Dudley M E. Adoptive cell transfer: a clinical path to effective cancer immunotherapy. Nature Reviews Cancer. 2008; 8(4):299-308. doi: doi:10.1038/nrc2355.

35. Katakura R, Suzuki Y, Sekine T, Sasaki Y F, Fujimiya Y. Therapeutic Efficacy of Adoptive Cell Transfer on Survival of Patients with Glioblastoma Multiforme: Case Reports. Case Reports in Oncology. 2010; 3(2):110-24. PubMed PMID: 20740183.

36. Hinrichs C S, Restifo N P. Reassessing target antigens for adoptive T-cell therapy. Nature Biotechnology. 2013; 31:999-1008. doi: doi:10.1038/nbt.2725.

37. Chmielewski M, Hombach A A, Abken H. Antigen-Specific T-Cell Activation Independently of the MEW: Chimeric Antigen Receptor-Redirected T Cells. Front Immunol. 2013; 4. doi: 10.3389/fimmu.2013.00371. PubMed PMID: 24273543; PubMed Central PMCID: PMC3822734.

38. Singh H, Huls H, Cooper L J. A new approach to gene therapy using Sleeping Beauty to genetically modify clinical-grade T cells to target CD19. 2014. doi: 10.1111/imr.12137.

39. Ivics Z, Hackett P B, Plasterk R H, Izsvak Z. Molecular reconstruction of Sleeping Beauty, a Tc1-like transposon from fish, and its transposition in human cells. Cell. 1997; 91(4):501-10. Epub Dec. 9, 1997. PubMed PMID: 9390559.

40. Maiti S, Huls H, Singh H, Dawson M, Figliola M, Olivares S, et al. Sleeping Beauty system to redirect T-cell specificity for human applications. 2013. doi: 10.1097/CJI.0b013e3182811ce9.

41. Kebriaei P, Huls H, Singh H, Olivares S, Figliola M, Kumar P R, et al. First Clinical Trials Employing Sleeping Beauty Gene Transfer System and Artificial Antigen Presenting Cells To Generate and Infuse T Cells Expressing CD19-Specific Chimeric Antigen Receptor. 2013.

42. Choi B D, Suryadevara C M, Gedeon P C, Herndon J E, 2nd, Sanchez-Perez L, Bigner D D, et al. Intracerebral delivery of a third generation EGFRvIII-specific chimeric antigen receptor is efficacious against human glioma. J Clin Neurosci. 2014; 21(1):189-90. Epub Sep. 24, 2013. doi: 10.1016/j.jocn.2013.03.012. PubMed PMID: 24054399; PubMed Central PMCID: PMCPMC3867597.

43. Han J, Chu J, Keung Chan W, Zhang J, Wang Y, Cohen J B, et al. CAR-Engineered NK Cells Targeting Wild-Type EGFR and EGFRvIII Enhance Killing of Glioblastoma and Patient-Derived Glioblastoma Stem Cells. Sci Rep. 2015; 5:11483. Epub Jul. 15, 2015. doi: 10.1038/srep11483. PubMed PMID: 26155832; PubMed Central PMCID: PMCPMC4496728.

44. Johnson L A, Sanchez-Perez L, Suryadevara C M, Sampson J H. Chimeric antigen receptor engineered T cells can eliminate brain tumors and initiate long-term protection against recurrence. Oncoimmunology. 32014.

45. Johnson L A, Scholler J, Ohkuri T, Kosaka A, Patel P R, McGettigan S E, et al. Rational development and characterization of humanized anti-EGFR variant III chimeric antigen receptor T cells for glioblastoma. Sci Transl Med. 2015; 7(275):275ra22. Epub Feb. 20, 2015. doi: 10.1126/scitranslmed.aaa4963. PubMed PMID: 25696001; PubMed Central PMCID: PMCPMC4467166.

46. Kong S, Sengupta S, Tyler B, Bais A J, Ma Q, Doucette S, et al. Suppression of Human Glioma Xenografts with Second-Generation IL13R-Specific Chimeric Antigen Receptor-Modified T Cells. 2012. doi: 10.1158/1078-0432.CCR-12-0319.

47. Miao H, Choi B D, Suryadevara C M, Sanchez-Perez L, Yang S, Leon G D, et al. EGFRvIII-Specific Chimeric Antigen Receptor T Cells Migrate to and Kill Tumor Deposits Infiltrating the Brain Parenchyma in an Invasive Xenograft Model of Glioblastoma. 2014. doi: 10.1371/journal.pone.0094281.

48. Morgan R A, Johnson L A, Davis J L, Zheng Z, Woolard K D, Reap E A, et al. Recognition of Glioma Stem Cells by Genetically Modified T Cells Targeting EGFRvIII and Development of Adoptive Cell Therapy for Glioma. 2012. doi: 10.1089/hum.2012.041.

49. Sampson J H, Choi B D, Sanchez-Perez L, Suryadevara C M, Snyder D J, Flores C T, et al. EGFRvIII mCAR-Modified T-Cell Therapy Cures Mice with Established Intracerebral Glioma and Generates Host Immunity against Tumor-Antigen Loss. 2014. doi: 10.1158/1078-0432.CCR-13-0709.

50. Shiina S, Ohno M, Ohka F, Kuramitsu S, Yamamichi A, Kato A, et al. CAR T Cells Targeting Podoplanin Reduce Orthotopic Glioblastomas in Mouse Brains. Cancer Immunol Res. 2016; 4(3):259-68. Epub Jan. 30, 2016. doi: 10.1158/2326-6066.cir-15-0060. PubMed PMID: 26822025.

51. Zhang C, Burger M C, Jennewein L, GenBler S, Schonfeld K, Zeiner P, et al. ErbB2/HER2-Specific NK Cells for Targeted Therapy of Glioblastoma. 2016. doi: 10.1093/jnci/djv375.

52. Shen C-J, Yang Y-X, Han E Q, Cao N, Wang Y-F, Wang Y, et al. Chimeric antigen receptor containing ICOS signaling domain mediates specific and efficient antitumor effect of T cells against EGFRvIII expressing glioma. 2013. doi: 10.1186/1756-8722-6-33.

53. Thaci B, Brown C E, Binello E, Werbaneth K, Sampath P, Sengupta S. Significance of interleukin-13 receptor alpha 2-targeted glioblastoma therapy. 2014. doi: 10.1093/neuonc/nou045.

54. Yaghoubi S S, Jensen M C, Satyamurthy N, Budhiraja S, Paik D, Czernin J, et al. Noninvasive detection of therapeutic cytolytic T cells with 18F-FHBG PET in a patient with glioma. Nat Clin Pract Oncol. 2009; 6(1):53-8. Epub Nov. 19, 2008. doi: 10.1038/ncponc1278. PubMed PMID: 19015650; PubMed Central PMCID: PMCPmc3526373.

55. Landi D, Center for Cell and Gene Therapy BCoM, USA, Hematology and Oncology TCsCC, USA, landi@bcm.edu, Hegde M, Center for Cell and Gene Therapy BCoM, USA, et al. Human Cytomegalovirus Antigens in Malignant Gliomas as Targets for Adoptive Cellular Therapy. Frontiers in Oncology. 2014; 4. doi: 10.3389/fonc.2014.00338.

56. Schuessler A, Smith C, Beagley L, Boyle G M, Rehan S, Matthews K, et al. Autologous T-cell Therapy for Cytomegalovirus as a Consolidative Treatment for Recurrent Glioblastoma. 2014. doi: 10.1158/0008-5472.CAN-14-0296.
57. Cheever M A, Allison J P, Ferris A S, Finn O J, Hastings B M, Hecht T T, et al. The Prioritization of Cancer Antigens: A National Cancer Institute Pilot Project for the Acceleration of Translational Research. 2009. doi: 10.1158/1078-0432.CCR-09-0737.
58. Driessche A V, Berneman Z N, Tendeloo VFIV. Active Specific Immunotherapy Targeting the Wilms' Tumor Protein 1 (WT1) for Patients with Hematological Malignancies and Solid Tumors: Lessons from Early Clinical Trials. 2012. doi: 10.1634/theoncologist.2011-0240.
59. Lindstedt I ea. The WT1 gene—its role in tumourigenesis and prospects for immunoth . . . —PubMed—NCBI. 2015.
60. Morgan R A ea. Cancer regression and neurological toxicity following anti-MAGE-A3 . . . —PubMed—NCBI. 2015.
61. Liu G, Ying H, Zeng G, Wheeler C J, Black K L, Yu J S. HER-2, gp100, and MAGE-1 Are Expressed in Human Glioblastoma and Recognized by Cytotoxic T Cells. 2004. doi: 10.1158/0008-5472.CAN-03-3504.
62. Ahmed N, Ratnayake M, Savoldo B, Perlaky L, Dotti G, Wels W S, et al. Regression of Experimental Medulloblastoma following Transfer of HER2-Specific T Cells. 2007. doi: 10.1158/0008-5472.CAN-06-4309.
63. Ahmed N, Salsman V S, Kew Y, Shaffer D, Powell S, Zhang Y J, et al. HER2-Specific T Cells Target Primary Glioblastoma Stem Cells and Induce Regression of Autologous Experimental Tumors. 2010. doi: 10.1158/1078-0432.CCR-09-1322.
64. Hegde M, Corder A, Chow K K, Mukherjee M, Ashoori A, Kew Y, et al. Combinational Targeting Offsets Antigen Escape and Enhances Effector Functions of Adoptively Transferred T Cells in Glioblastoma. Molecular Therapy. 2013; 21(11):2087-101. doi: doi:10.1038/mt.2013.185.
65. Cross D, Burmester J K. Gene Therapy for Cancer Treatment: Past, Present and Future. 2006. doi: 10.3121/cmr.4.3.218.
66. Kuriyama S, Third Department of Internal Medicine NMU, Kashihara, Nara, Japan, Third Department of Internal Medicine NMU, 840 Shijo-cho, Kashihara, Nara 634-8522, Japan. Fax: (81)744-24-7122., Kikukawa M, Third Department of Internal Medicine NMU, Kashihara, Nara, Japan, Masui K, et al. Cancer gene therapy with HSV-tk/GCV system depends on t-cell-mediated immune responses and causes apoptotic death of tumor cells In vivo. International Journal of Cancer. 83(3): 374-80. doi: 10.1002/(SICI)1097-0215(19991029)83:3<374::AID-IJC13>3.0.CO; 2-#.
67. Immonen A, Vapalahti M, Tyynel K, [auml], Hurskainen H, Sandmair A, et al. AdvHSV-tk Gene Therapy with Intravenous Ganciclovir Improves Survival in Human Malignant Glioma: A Randomised, Controlled Study. Molecular Therapy. 2004; 10(5):967-72. doi: doi: 10.1016/j.ymthe.2004.08.002.
68. Ryu C H, Park K Y, Kim S M, Jeong C H, Woo J S, Hou Y, et al. Valproic acid enhances anti-tumor effect of mesenchymal stem cell mediated HSV-TK gene therapy in intracranial glioma. Biochem Biophys Res Commun. 2012; 421(3):585-90. Epub Apr. 25, 2012. doi: 10.1016/j.bbrc.2012.04.050. PubMed PMID: 22525671.
69. Li S, Gu C, Gao Y, Amano S, Koizumi S, Tokuyama T, et al. Bystander effect in glioma suicide gene therapy using bone marrow stromal cells. Stem Cell Res. 2012; 9(3):270-6. Epub Oct. 2, 2012. doi: 10.1016/j.scr.2012.08.002. PubMed PMID: 23022734.
70. Amano S, Gu C, Koizumi S, Tokuyama T, Namba H. Tumoricidal bystander effect in the suicide gene therapy using mesenchymal stem cells does not injure normal brain tissues. Cancer Lett. 2011; 306(1):99-105. Epub Apr. 1, 2011. doi: 10.1016/j.canlet.2011.02.037. PubMed PMID: 21450400.
71. Pu K, Li S Y, Gao Y, Ma L, Ma W, Liu Y. Bystander effect in suicide gene therapy using immortalized neural stem cells transduced with herpes simplex virus thymidine kinase gene on medulloblastoma regression. Brain Res. 2011; 1369:245-52. Epub Nov. 16, 2010. doi: 10.1016/j.brainres.2010.10.107. PubMed PMID: 21073865.
72. Namba H, Kawaji H, Yamasaki T. Use of genetically engineered stem cells for glioma therapy. Oncol Lett. 112016. p. 9-15.
73. DiMeco F, Rhines L D, Hanes J, Tyler B M, Brat D, Torchiana E, et al. Paracrine delivery of IL-12 against intracranial 9 L gliosarcoma in rats. J Neurosurg. 2000; 92(3):419-27. Epub Mar. 4, 2000. doi: 10.3171/jns.2000.92.3.0419. PubMed PMID: 10701528.
74. Kikuchi T, Joki T, Saitoh S, Hata Y, Abe T, Kato N, et al. Anti-tumor activity of interleukin-2-producing tumor cells and recombinant interleukin 12 against mouse glioma cells located in the central nervous system. Int J Cancer. 1999; 80(3):425-30. Epub Feb. 6, 1999. PubMed PMID: 9935185.
75. Ehtesham M, Kabos P, Kabosova A, Neuman T, Black K L, Yu J S. The use of interleukin 12-secreting neural stem cells for the treatment of intracranial glioma. Cancer Res. 2002; 62(20):5657-63. Epub Oct. 18, 2002. PubMed PMID: 12384520.
76. Jean W C, Spellman S R, Wallenfriedman M A, Hall W A, Low W C. Interleukin-12-based immunotherapy against rat 9 L glioma. Neurosurgery. 1998; 42(4):850-6; discussion 6-7. Epub May 9, 1998. PubMed PMID: 9574650.
77. Wallenfriedman M A, Conrad J A, DelaBarre L, Graupman P C, Lee G, Garwood M, et al. Effects of continuous localized infusion of granulocyte-macrophage colony-stimulating factor and inoculations of irradiated glioma cells on tumor regression. J Neurosurg. 1999; 90(6):1064-71. Epub Jun. 1, 1999. doi: 10.3171/jns.1999.90.6.1064. PubMed PMID: 10350253.
78. Liu Y, Ng K, Lillehei K O. Time course analysis and modulating effects of established brain tumor on active-specific immunotherapy. Neurosurg Focus. 2000; 9(6):e3. Epub Jul. 5, 2006. PubMed PMID: 16817686.
79. Prins R M, Odesa S K, Liau L M. Immunotherapeutic targeting of shared melanoma-associated antigens in a murine glioma model. Cancer Res. 2003; 63(23):8487-91. Epub Dec. 18, 2003. PubMed PMID: 14679014.
80. Jean W C, Spellman S R, Wallenfriedman M A, Flores C T, Kurtz B P, Hall W A, et al. Effects of combined granulocyte-macrophage colony-stimulating factor (GM-CSF), interleukin-2, and interleukin-12 based immunotherapy against intracranial glioma in the rat. J Neurooncol. 2004; 66(1-2):39-49. Epub Mar. 16, 2004. PubMed PMID: 15015768.
81. Wollmann G, Ozduman K, van den Pol A N. Oncolytic virus therapy for glioblastoma multiforme: concepts and candidates. Cancer J. 2012; 18(1):69-81. Epub Feb. 1, 2012. doi: 10.1097/PPO.0b013e31824671c9. PubMed PMID: 22290260; PubMed Central PMCID: PMCPMC3632333.

82. Goetz C, Dobrikova E, Shveygert M, Dobrikov M, Gromeier M. Oncolytic poliovirus against malignant glioma. Future Virol. 2011; 6(9):1045-58. doi: 10.2217/fv1.11.76. PubMed PMID: 21984883; PubMed Central PMCID: PMC3187927.

83. Chaffey N. Alberts, B., Johnson, A., Lewis, J., Raff, M., Roberts, K. and Walter, P. Molecular biology of the cell. 4th edn. Ann Bot. 2003; 91(3):401. doi: 10.1093/aob/mcg023. PubMed Central PMCID: PMC4244961.

84. Nakai R, Maniwa Y, Tanaka Y, Nishio W, Yoshimura M, Okita Y, et al. Overexpression of Necl-5 correlates with unfavorable prognosis in patients with lung adenocarcinoma. Cancer Sci. 2010; 101(5):1326-30. Epub Maar. 25, 2010. doi: 10.1111/j.1349-7006.2010.01530.x. PubMed PMID: 20331633.

85. Castriconi R, Daga A, Dondero A, Zona G, Poliani P L, Melotti A, et al. N K Cells Recognize and Kill Human Glioblastoma Cells with Stem Cell-Like Properties. 2009. doi: 10.4049/jimmunol.0802845.

86. Campbell S A, Lin J, Dobrikova E Y, Gromeier M. Genetic Determinants of Cell Type-Specific Poliovirus Propagation in HEK 293 Cells. J Virol. 792005. p. 6281-90.

87. Gromeier M, Alexander L, Wimmer E. Internal ribosomal entry site substitution eliminates neurovirulence in intergeneric poliovirus recombinants. Proc Natl Acad Sci USA. 1996; 93(6):2370-5. Epub Maar. 19, 1996. PubMed PMID: 8637880; PubMed Central PMCID: PMCPMC39803.

88. Gromeier M, Solecki D, Patel D D, Wimmer E. Expression of the human poliovirus receptor/CD155 gene during development of the central nervous system: implications for the pathogenesis of poliomyelitis. Virology. 2000; 273(2):248-57. Epub Aug. 1, 2000. doi: 10.1006/viro.2000.0418. PubMed PMID: 10915595.

89. Gromeier M, Lachmann S, Rosenfeld M R, Gutin P H, Wimmer E. Intergeneric poliovirus recombinants for the treatment of malignant glioma. Proc Natl Acad Sci USA. 2000; 97(12):6803-8. Epub Jun. 7, 2000. PubMed PMID: 10841575; PubMed Central PMCID: PMCPMC18745.

90. Merrill M K, Bernhardt G, Sampson J H, Wikstrand C J, Bigner D D, Gromeier M. Poliovirus receptor CD155-targeted oncolysis of glioma. Neuro Oncol. 2004; 6(3):208-17. Epub Jul. 29, 2004. doi: 10.1215/s1152851703000577. PubMed PMID: 15279713; PubMed Central PMCID: PMCPMC1871993.

91. Dobrikova E Y, Broadt T, Poiley-Nelson J, Yang X, Soman G, Giardina S, et al. Recombinant oncolytic poliovirus eliminates glioma in vivo without genetic adaptation to a pathogenic phenotype. Mol Ther. 2008; 16(11):1865-72. doi: 10.1038/mt.2008.184. PubMed PMID: 18766173; PubMed Central PMCID: PMC2856473.

92. Levitan D. Polio-Rhinovirus Conjugate Shows Promise in Early Recurrent Glioblastoma Trial 2014. Available from: http://www.cancernetwork.com/sno-2014/polio-rhinovirus-conjugate-shows-promise-early-recurrent-glioblastoma-trial.

93. Feller S. Poliovirus therapy against cancer given 'breakthrough' status by FDA2016. Available from: http://www.upi.com/Health News/2016/05/17/Poliovirus-therapy-against-cancer-given-breakthrough-status-by-FDA/6541463499960/.

94. Alemany R, Balague C, Curiel D T. Replicative adenoviruses for cancer therapy. Nat Biotechnol. 2000; 18(7):723-7. Epub Jul. 11, 2000. doi: 10.1038/77283. PubMed PMID: 10888838.

95. Wohlfahrt M E, Beard B C, Lieber A, Kiem H P. A capsid-modified, conditionally replicating oncolytic adenovirus vector expressing TRAIL Leads to enhanced cancer cell killing in human glioblastoma models. Cancer Res. 2007; 67(18):8783-90. Epub Sep. 19, 2007. doi: 10.1158/0008-5472.can-07-0357. PubMed PMID: 17875719.

96. Toth K, Dhar D, Wold W S. Oncolytic (replication-competent) adenoviruses as anticancer agents. Expert Opin Biol Ther. 2010; 10(3):353-68. Epub Feb. 6, 2010. doi: 10.1517/14712590903559822. PubMed PMID: 20132057.

97. Chiocca E A, Aguilar L K, Bell S D, Kaur B, Hardcastle J, Cavaliere R, et al. Phase D3 Study of Gene-Mediated Cytotoxic Immunotherapy Adjuvant to Up-Front Surgery and Intensive Timing Radiation for Malignant Glioma. 2011. doi: 10.1200/JCO.2011.35.5222.

98. Dorig R E, Marcil A, Chopra A, Richardson C D. The human CD46 molecule is a receptor for measles virus (Edmonston strain). Cell. 1993; 75(2):295-305. Epub Oct. 22, 1993. PubMed PMID: 8402913.

99. Jurianz K, Ziegler S, Garcia-Schuler H, Kraus S, Bohana-Kashtan O, Fishelson Z, et al. Complement resistance of tumor cells: basal and induced mechanisms. Mol Immunol. 1999; 36(13-14):929-39. Epub Mar. 4, 2000. PubMed PMID: 10698347.

100. Galanis E, Bateman A, Johnson K, Diaz R M, James C D, Vile R, et al. Use of viral fusogenic membrane glycoproteins as novel therapeutic transgenes in gliomas. Hum Gene Ther. 2001; 12(7):811-21. Epub May 8, 2001. doi: 10.1089/104303401750148766. PubMed PMID: 11339897.

101. Phuong L K, Allen C, Peng K W, Giannini C, Greiner S, TenEyck C J, et al. Use of a vaccine strain of measles virus genetically engineered to produce carcinoembryonic antigen as a novel therapeutic agent against glioblastoma multiforme. Cancer Res. 2003; 63(10):2462-9. Epub May 17, 2003. PubMed PMID: 12750267.

102. Reinhart B, Mazzacurati L, Forero A, Hong C S, Eguchi J, Okada H, et al. Inhibition of Indoleamine-2,3-dioxygenase (IDO) in Glioblastoma Cells by Oncolytic Herpes Simplex Virus. Adv Virol. 2012; 2012:815465. Epub Aug. 28, 2012. doi: 10.1155/2012/815465. PubMed PMID: 22924042; PubMed Central PMCID: PMCPMC3424635.

103. Castle J C, Kreiter S, Diekmann J, Löwer M, Roemer Nvd, Graaf Jd, et al. Exploiting the Mutanome for Tumor Vaccination. 2012. doi: 10.1158/0008-5472.CAN-11-3722.

104. Iyer G, Hanrahan A J, Milowsky M I, Al-Ahmadie H, Scott S N, Janakiraman M, et al. Genome Sequencing Identifies a Basis for Everolimus Sensitivity. 2012. doi: 10.1126/science.1226344.

105. Gerlinger M, Rowan A J, Horswell S, Larkin J, Endesfelder D, Gronroos E, et al. Intratumor heterogeneity and branched evolution revealed by multiregion sequencing. N Engl J Med. 2012; 366(10):883-92. Epub Mar. 9, 2012. doi: 10.1056/NEJMoa1113205. PubMed PMID: 22397650.

106. Stieber D, Golebiewska A, Evers L, Lenkiewicz E, Brons N H, Nicot N, et al. Glioblastomas are composed of genetically divergent clones with distinct tumourigenic potential and variable stem cell-associated phenotypes. Acta Neuropathol. 2014; 127(2):203-19. Epub Oct. 25, 2013. doi: 10.1007/s00401-013-1196-4. PubMed PMID: 24154962; PubMed Central PMCID: PMCPmc3895194.

107. Wheler J, Lee J J, Kurzrock R. Unique molecular landscapes in cancer: implications for individualized, curated drug combinations. Cancer Res. 2014; 74(24): 7181-4. Epub Oct. 19, 2014. doi: 10.1158/0008-5472.can-14-2329. PubMed PMID: 25326492; PubMed Central PMCID: PMCPmc4292868.

108. Kurzrock R, Giles F J. Precision Oncology for Patients with Advanced Cancer: The Challenges of Malignant Snowflakes. Cell Cycle. 2015:0. Epub Jun. 2, 2015. doi: 10.1080/15384101.2015.1041695. PubMed PMID: 26030337.

109. Krogan N J ea. The Cancer Cell Map Initiative: Defining the Hallmark Networks of Cancer.—PubMed—NCBI. 2015.

110. Sampson J H, Archer G E, Mitchell D A, Heimberger A B, Herndon J E, 2nd, Lally-Goss D, et al. An epidermal growth factor receptor variant III-targeted vaccine is safe and immunogenic in patients with glioblastoma multiforme. Mol Cancer Ther. 8. United States 2009. p. 2773-9.

111. Sampson J H, Heimberger A B, Archer G E, Aldape K D, Friedman A H, Friedman H S, et al. Immunologic Escape After Prolonged Progression-Free Survival With Epidermal Growth Factor Receptor Variant III Peptide Vaccination in Patients With Newly Diagnosed Glioblastoma. 2010. doi: 10.1200/JCO.2010.28.6963.

112. Sampson J H, Akabani G, Archer G E, Berger M S, Coleman R E, Friedman A H, et al. Intracerebral infusion of an EGFR-targeted toxin in recurrent malignant brain tumors. Neuro Oncol. 10. United States 2008. p. 320-9.

113. Linna Li, Tony S. Quang, Ed J. Gracely, Ji H. Kim, Jacqueline G. Emrich, Theodore E. Yaeger, et al. A Phase II study of anti-epidermal growth factor receptor radio-immunotherapy in the treatment of glioblastoma multiforme. http://dxdoiorg/103171/20102JNS091211. 2010. doi: 2010.2.JNS091211.

114. Prins R M, Soto H, Konkankit V, Odesa S K, Eskin A, Yong W H, et al. Gene Expression Profile Correlates with T-Cell Infiltration and Relative Survival in Glioblastoma Patients Vaccinated with Dendritic Cell Immunotherapy. 2011. doi: 10.1158/1078-0432.CCR-10-2563.

115. Fong B, Department of Neurosurgery DGSoMaU, University of California Los Angeles, Los Angeles, Calif., United States of America, Jin R, Department of Neurosurgery DGSoMaU, University of California Los Angeles, Los Angeles, Calif., United States of America, Wang X, Department of Biostatistics DGSoMaU, University of California Los Angeles, Los Angeles, Calif., United States of America, et al. Monitoring of Regulatory T Cell Frequencies and Expression of CTLA-4 on T Cells, before and after DC Vaccination, Can Predict Survival in GBM Patients. PLOS ONE. 2012; 7(4). doi: 10.1371/journal.pone.0032614.

116. Denise A. Caruso L M O, Alana M. Neale, Fiona J. Radcliff, Gerlinda M. Amor, Wirginia Maixner, Peter Downie, Timothy E. Hassall, Mimi L. K. Tang, David M. Ashley. Results of a phase 1 study utilizing monocyte-derived dendritic cells pulsed with tumor RNA in children and young adults with brain cancer. Neuro-Oncology. 2004; 6(3):236-46. doi: 10.1215/S1152851703000668. PubMed Central PMCID: PMCPMC1872001.

117. Yu J S, Wheeler C J, Zeltzer P M, Ying H, Finger D N, Lee P K, et al. Vaccination of Malignant Glioma Patients with Peptide-pulsed Dendritic Cells Elicits Systemic Cytotoxicity and Intracranial T-cell Infiltration. 2001.

118. Yu J S, Liu G, Ying H, Yong W H, Black K L, Wheeler C J. Vaccination with Tumor Lysate-Pulsed Dendritic Cells Elicits Antigen-Specific, Cytotoxic T-Cells in Patients with Malignant Glioma. 2004. doi: 10.1158/0008-5472.CAN-03-3505.

119. Yamanaka R, Abe T, Yajima N, Tsuchiya N, Homma J, Kobayashi T, et al. Vaccination of recurrent glioma patients with tumour lysate-pulsed dendritic cells elicits immune responses: results of a clinical phase I|[sol]|II trial. British Journal of Cancer. 2003; 89(7):1172-9. doi: doi:10.1038/sj.bjc.6601268.

120. Galanis E, Buckner J C, Maurer M J, Kreisberg J I, Ballman K, Boni J, et al. Phase II Trial of Temsirolimus (CCI-779) in Recurrent Glioblastoma Multiforme: A North Central Cancer Treatment Group Study. 2005. doi: 10.1200/JCO.2005.23.622.

121. Lee E Q, Kuhn J, Lamborn K R, Abrey L, Deangelis L M, Lieberman F, et al. Phase I/II study of sorafenib in combination with temsirolimus for recurrent. Neuro Oncol. 2012; 14(12):1511-8. Epub Oct. 27, 2012. doi: 10.1093/neuonc/nos264. PubMed PMID: 23099651; PubMed Central PMCID: PMCPmc3499017.

122. Chang S M, Wen P, Cloughesy T, Greenberg H, Schiff D, Conrad C, et al. Phase II study of CCI-779 in patients with recurrent glioblastoma multiforme. Invest New Drugs. 2005; 23(4):357-61. Epub Jul. 14, 2005. doi: 10.1007/s10637-005-1444-0. PubMed PMID: 16012795.

123. Germano I M, Fable J, Humayun Gultekin S, Silvers A. Adenovirus/Herpes Simplex-Thymidine Kinase/Ganciclovir Complex: Preliminary Results of a Phase I trial in Patients with Recurrent Malignant Gliomas. Journal of Neuro-Oncology. 2003; 65(3). Epub 289. doi: 10.10238:NEON.0000003657.95085.56.

124. Shand N, Weber F, Mariani L, Bernstein M, Gianella-Borradori A, Long Z, et al. A Phase 1-2 Clinical Trial of Gene Therapy for Recurrent Glioblastoma Multiforme by Tumor Transduction with the Herpes Simplex Thymidine Kinase Gene Followed by Ganciclovir. http://dxdoiorg/101089/10430349950016979. 2004. doi: 1043-0342(19990920)10:14L.2325; 1-.

125. Rainov N G. A Phase III Clinical Evaluation of Herpes Simplex Virus Type 1 Thymidine Kinase and Ganciclovir Gene Therapy as an Adjuvant to Surgical Resection and Radiation in Adults with Previously Untreated Glioblastoma Multiforme. http://dxdoiorg/101089/104303400750038499. 2004. doi: 1043-0342(20001120) 11:17L.2389; 1-.

126. Poliovirus Vaccine for Recurrent Glioblastoma Multiforme (GBM)—Full Text View—ClinicalTrials.gov 2012. Available from: http://clinicaltrials.gov/ct2/show/NCT01491893?term=NCT01491893&rank=1.

127. Lillehei K O, Mitchell D H, Johnson S D, McCleary E L, Kruse C A. Long-term follow-up of patients with recurrent malignant gliomas treated with adjuvant adoptive immunotherapy. Neurosurgery. 1991; 28(1):16-23. Epub Jan. 1, 1991. PubMed PMID: 1994273.

128. Sankhla S K, Hospital T M, Nadkarni J S, Hospital T M, Bhagwati S N, Hospital T M. Adoptive immunotherapy using lymphokine-activated killer (LAK) cells and interleukin-2 for recurrent malignant primary brain tumors. Journal of Neuro-Oncology. 2013; 27(2):133-40. doi: 10.1007/BF00177476.

129. Hayes R L, Departments of Neurosurgery KCCC, New York University Medical Center, New York, N.Y., N.Y. University Medical Center NoLR, 550 First Avenue, New York, N.Y. 10016, Koslow M, Department of Microbiology KCCC, New York University Medical Center, New York, N.Y., Hiesiger E M, et al. Improved long term survival after intracavitary interleukin-2 and lymphokine-activated killer cells for adults with recurrent malignant glioma. Cancer. 76(5): 840-52. doi: 10.1002/1097-0142 (19950901)76:5<840::AID-CNCR2820760519>3.0.CO; 2-R.
130. Dillman R O, Duma C M, Schiltz P M, DePriest C, Ellis R A, Okamoto K, et al. Intracavitary Placement of Autologous Lymphokine-Activated Killer (LAK) Cells after Resection of Recurrent Glioblastoma. Journal of Immunotherapy. 2004; 27(5):398-44.
131. Plautz G E, Miller D W, Barnett G H, Stevens G H J, Maffett S, Kim J, et al. T Cell Adoptive Immunotherapy of Newly Diagnosed Gliomas. 2000.
132. Jacobs S K, Wilson D J, Kornblith P L, Grimm E A. Interleukin-2 or Autologous Lymphokine-activated Killer Cell Treatment of Malignant Glioma: Phase I Trial. 1986.
133. David Barba, Stephen C. Saris, Carol Holder, Steven A. Rosenberg, Edward H. Oldfield. Intratumoral LAK cell and interleukin-2 therapy of human gliomas. http://dx-doiorg/103171/jns19897020175. 1989. doi: 10.3171/jns.1989.70.2.0175.
134. Boiardi A, Besta" INNC, Silvani A, Besta" INNC, Ruffini P A, Tumori I Nd, et al. Loco-regional immunotherapy with recombinant interleukin-2 and adherent lymphokine-activated killer cells (A-LAK) in recurrent glioblastoma patients. Cancer Immunology, Immunotherapy. 2013; 39(3):193-7. doi: 10.1007/BF01533386.

ADDITIONAL REFERENCES

Barkovich, A. J., Guerrini, R., Kuzniecky, R. I., Jackson, G. D., and Dobyns, W. B. A developmental and genetic classification for malformations of cortical development: update 2012.

Bhattacharyya, S., Zagó Rska, A., Lew, E. D., Shrestha, B., Rothlin, C. V, Naughton, J., Diamond, M. S., Lemke, G., and Young, J. A. T. (2013). Enveloped Viruses Disable Innate Immune Responses in Dendritic Cells by Direct Activation of TAM Receptors.

Bond, J., Roberts, E., Springell, K., Lizarraga, S., Scott, S., Higgins, J., Hampshire, D. J., Morrison, E. E., Leal, G. F., Silva, E. O., et al. (2005). A centrosomal mechanism involving CDK5RAP2 and CENPJ controls brain size. Nat. Genet. 37, 353-355.

Bowen, J. R., Quicke, K. M., Maddur, M. S., O'Neal, J. T., McDonald, C. E., Fedorova, N. B., Puri, V., Shabman, R. S., Pulendran, B., and Suthar, M. S. (2017). Zika Virus Antagonizes Type I Interferon Responses during Infection of Human Dendritic Cells. PLoS Pathog. 13, e1006164.

Bulstrode, H., Johnstone, E., Marques-Torrejon, M. A., Ferguson, K. M., Bressan, R. B., Blin, C., Grant, V., Gogolok, S., Gangoso, E., Gagrica, S., et al. Elevated FOXG1 and SOX2 in glioblastoma enforces neural stem cell identity through transcriptional control of cell cycle and epigenetic regulators.

Chakraborty, S. (2016). Computational analysis of perturbations in the post-fusion Dengue virus envelope protein highlights known epitopes and conserved residues in the Zika virus. F1000 Research 5, 1150.

Cizmecioglu, O., Arnold, M., Bahtz, R., Settele, F., Ehret, L., Haselmann-Weiß, U., Antony, C., and Hoffmann, I. (2010). Cep152 acts as a scaffold for recruitment of Plk4 and CPAP to the centrosome. J. Cell Biol. 191.

Coutard, B., Banal, K., Lichière, J., Selisko, B., Martin, B., Aouadi, W., Lombardia, M. O., Debart, F., Vasseur, J.-J., Guillemot, J. C., et al. (2017). Zika Virus Methyltransferase: Structure and Functions for Drug Design Perspectives. J. Virol. 91, e02202-16.

Cunha, M. S., Esposito, D. L. A., Rocco, I. M., Maeda, A. Y., Vasami, F. G. S., Nogueira, J. S., de Souza, R. P., Suzuki, A., Addas-Carvalho, M., Barj as-Castro, M. de L., et al. (2016). First Complete Genome Sequence of Zika Virus (Flaviviridae, Flavivirus) from an Autochthonous Transmission in Brazil. Genome Announc. 4, e00032-16.

Dang, J., Tiwari, S. K., Lichinchi, G., Qin, Y., Patil, V. S., Eroshkin, A. M., and Rana, T. M. (2016). Zika Virus Depletes Neural Progenitors in Human Cerebral Organoids through Activation of the Innate Immune Receptor TLR3.

Dick, G. W., Kitchen, S. F. & Haddow, A. J. Zika virus. I. Isolations and serological specificity. Trans. R. Soc. Trop. Med. Hyg 46, 509-520 (1952).

Frayling, T. M., Timpson, N.J., Weedon, M. N., Zeggini, E., Freathy, R. M., Lindgren, C. M., Perry, J. R. B., Elliott, K. S., Lango, H., Rayner, N. W., et al. (2007). A Common Variant in the FTO Gene Is Associated with Body Mass Index and Predisposes to Childhood and Adult Obesity. Science (80-.). 316.

Gabriel, E., Ramani, A., Karow, U., Gottardo, M., Natarajan, K., Gooi, L. M., Goranci-Buzhala, G., Krut, O., Peters, F., Nikolic, M., et al. (2017). Recent Zika Virus Isolates Induce Premature Differentiation of Neural Progenitors in Human Brain Organoids.

Grant, A., Ponia, S. S., Tripathi, S., Balasubramaniam, V., Miorin, L., Sourisseau, M., Schwarz, M. C., Sánchez-Seco, M. P., Evans, M. J., Best, S. M., et al. (2016). Zika Virus Targets Human STAT2 to Inhibit Type I Interferon Signaling.

Guernsey, D. L., Jiang, H., Hussin, J., Arnold, M., Bouyakdan, K., Perry, S., Babineau-Sturk, T., Beis, J., Dumas, N., Evans, S. C., et al. (2010). ARTICLE Mutations in Centrosomal Protein CEP152 in Primary Microcephaly Families Linked to MCPH4.

Heymann, D. L., Hodgson, A., Alpha Sall, A., Freedman, D. O., Erin Staples, J., Althabe, F., Baruah, K., Mahmud, G., Kandun, N., C Vasconcelos, P. F., et al. (2016). Zika virus and microcephaly: why is this situation a PHEIC? Lancet 387, 719-721.

Hu, J. K.-H., Du, W., Shelton, S. J., Oldham, M. C., DiPersio, C. M., and Klein, O. D. (2017). An FAK-YAP-mTOR Signaling Axis Regulates Stem Cell-Based Tissue Renewal in Mice. Cell Stem Cell.

Jabado, N., Jankowski, A., Dougaparsad, S., Picard, V., Grinstein, S., and Gros, P. (2000). Natural Resistance to Intracellular Infections. J. Exp. Med. 192.

Jia, G., Fu, Y., Zhao, X., Dai, Q., Zheng, G., Yang, Y., Yi, C., Lindahl, T., Pan, T., Yang, Y.-G., et al. (2011). N6-Methyladenosine in nuclear RNA is a major substrate of the obesity-associated FTO.

Kim, S. Y., Zhao, J., Liu, X., Fraser, K., Lin, L., Zhang, X., Zhang, F., Dordick, J. S., and Linhardt, R. J. (2017). Interaction of Zika Virus Envelope Protein with Glycosaminoglycans. Biochemistry 56, 1151-1162.

Kleber de Oliveira, W., Cortez-Escalante, J., De Oliveira, W. T. G. H., do Carmo, G. M. I., Henriques, C. M. P., Coelho, G. E., and Araújo de Franca, G. V. (2016). Increase in Reported Prevalence of Microcephaly in Infants Born to Women Living in Areas with Confirmed Zika Virus Transmission During the First Trimester of Pregnancy—Brazil, 2015. MMWR. Morb. Mortal. Wkly. Rep. 65.

Li, H., Saucedo-Cuevas, L., Regla-Nava, J. A., Chai, G., Sheets, N., Tang, W., Terskikh, A. V., Shresta, S., and Gleeson, J. G. (2016). Zika Virus Infects Neural Progenitors in the Adult Mouse Brain and Alters Proliferation.

Liang, Q., Luo, Z., Zeng, J., Chen, W., Foo, S.-S., Lee, S.-A., Ge, J., Wang, S., Goldman, S. A., Zlokovic, B. V., et al. (2016). Zika Virus NS4A and NS4B Proteins Deregulate Akt-mTOR Signaling in Human Fetal Neural Stem Cells to Inhibit Neurogenesis and Induce Autophagy.

Lichinchi, G., Zhao, B. S., Wu, Y., Lu, Z., Qin, Y., He, C., and Rana, T. M. (2016). Dynamics of Human and Viral RNA Methylation during Zika Virus Infection.

Lindenbach, B. D., and Rice, C. M. (2003). Molecular biology of flaviviruses. Adv. Virus Res. 59, 23-61.

Lui, V. W. et al. Frequent mutation of the PI3K pathway in head and neck cancer defines predictive biomarkers. Cancer Discov. 3, 761-769 (2013).

Meertens, L., Carnec, X., Lecoin, M. P., Ramdasi, R., Guivel-Benhassine, F., Lew, E., Lemke, G., Schwartz, O., and Amara, A. (2012). The TIM and TAM Families of Phosphatidylserine Receptors Mediate Dengue Virus Entry.

Meertens, L., Labeau, A., Dejarnac, O., Cipriani, S., Sinigaglia, L., Bonnet-Madin, L., Le Charpentier, T., Hafirassou, M. L., Zamborlini, A., Cao-Lormeau, V.-M., et al. (2017). Axl Mediates ZIKA Virus Entry in Human Glial Cells and Modulates Innate Immune Responses.

Miller, E., Becker, Z., Shalev, D., Lee, C. T., Cioroiu, C., and Thakur, K. (2017). Probable Zika virus-associated Guillain-Barré syndrome: Challenges with clinico-laboratory diagnosis.

Modis, Y., Ogata, S., Clements, D., and Harrison, S. C. Structure of the dengue virus envelope protein after membrane fusion.

Nowakowski, T. J., Pollen, A. A., Di Lullo, E., Sandoval-Espinosa, C., Bershteyn, M., and Kriegstein, A. R. (2016). Expression Analysis Highlights AXL as a Candidate Zika Virus Entry Receptor in Neural Stem Cells.

Oehler, E., Watrin, L., Lane, P., Leparc-Goffart, I., Lastère, S., Valour, F., Baudouin, L., Mallet, H., Musso, D., and Ghawche, F. (2014). Zika virus infection complicated by Guillain-Barré syndrome—case report, French Polynesia, December 2013. Eurosurveillance 19, 20720.

Rauch, A., Thiel, C. T., Schindler, D., Wick, U., Crow, Y. J., Ekici, A. B., van Essen, A. J., Goecke, T. O., Al-Gazali, L., Chrzanowska, K. H., et al. (2008). Mutations in the Pericentrin (PCNT) Gene Cause Primordial Dwarfism. Science (80-.). 319.

Retallack, H., Lullo, E. Di, Arias, C., Knopp, K. A., Laurie, M. T., Sandoval-Espinosa, C., Leon, W. R. M., Krencik, R., Ullian, E. M., Spatazza, J., et al. Zika virus cell tropism in the developing human brain and inhibition by azithromycin.

Rothlin, C. V, Ghosh, S., Zuniga, E. I., Oldstone, M. B. A., and Lemke, G. TAM Receptors Are Pleiotropic Inhibitors of the Innate Immune Response.

Samuels, Y. & Ericson, K. Oncogenic PI3K and its role in cancer. Curr. Opin. Oncol. 18, 77-82 (2006).

Song, M. S., Salmena, L. & Pandolfi, P. P. The functions and regulation of the PTEN tumour suppressor. Nature Rev. Mol. Cell Biol. 13, 283-296 (2012).

Souza, B. S. F., Sampaio, G. L. A., Pereira, C. S., Campos, G. S., Sardi, S. I., Freitas, L. A. R., Figueira, C. P., Paredes, B. D., Nonaka, C. K. V., Azevedo, C. M., et al. (2016). Zika virus infection induces mitosis abnormalities and apoptotic cell death of human neural progenitor cells. Sci. Rep. 6, 39775.

Stephen, P., Baz, M., Boivin, G., and Lin, S.-X. (2016). Structural Insight into NS5 of Zika Virus Leading to the Discovery of MTase Inhibitors. J. Am. Chem. Soc. 138, 16212-16215.

Tang, H., Hammack, C., Ogden, S. C., Wen, Z., Qian, X., Li, Y., Yao, B., Shin, J., Zhang, F., Lee, E. M., et al. (2016). Zika Virus Infects Human Cortical Neural Progenitors and Attenuates Their Growth.

Wells, M. F., Salick, M. R., Wiskow, O., Ho, D. J., Worringer, K. A., Ihry, R. J., Kommineni, S., Bilican, B., Klim, J. R., Hill, E. J., et al. (2016). Genetic Ablation of AXL Does Not Protect Human Neural Progenitor Cells and Cerebral Organoids from Zika Virus Infection.

Zheng, G., Dahl, J. A., Niu, Y., Fedorcsak, P., Huang, C.-M., Li, C. J., Vå, C. B., Shi, Y., Wang, W.-L., Song, S.-H., et al. (2013). ALKBH5 Is a Mammalian RNA Demethylase that Impacts RNA Metabolism and Mouse Fertility.

Hwang M L et al., J Immunol, 179:5829-5838, 2007

Tran C T et al., Neuropathology and Applied Neurobiology, 24:293-301, 1998

We claim:

1. An anti-tumor composition comprising Zika virus, a carrier suitable for direct intra-tumoral delivery, and a cancer vaccine.

2. The anti-tumor composition of claim 1, wherein the vaccine comprises irradiated autologous glioblastoma multiforme (GBM) tumor cells previously infected with the Zika virus.

3. The anti-tumor composition of claim 2, wherein the vaccine is administered with the cytokine granulocyte-macrophage colony-stimulating factor (GM-CSF).

4. The anti-tumor composition of claim 1, wherein the vaccine comprises irradiated allogeneic GBM tumor cells previously infected with the Zika virus.

5. The anti-tumor composition of claim 4, wherein the vaccine is administered with the cytokine GM-CSF.

6. The anti-tumor composition of claim 4, wherein the vaccine comprises irradiated allogenic tumor cells of the classical GBM phenotype previously infected with the Zika virus.

7. The anti-tumor composition of claim 4, wherein the vaccine comprises irradiated allogenic tumor cells of the mesenchymal GBM phenotype previously infected with the Zika virus.

8. The anti-tumor composition of claim 4, wherein the vaccine comprises irradiated allogenic tumor cells of the proneural GBM phenotype previously infected with the Zika virus.

9. The anti-tumor composition of claim 4, wherein the vaccine comprises irradiated allogeneic tumor cells of the neural GBM phenotype previously infected with the Zika virus.

10. The anti-tumor composition of claim 4, wherein the vaccine comprises irradiated allogeneic tumor cells of any combination of classical, mesenchymal, proneural, and/or neural GBM phenotype previously infected with the Zika virus.

11. The anti-tumor composition of claim 4, wherein the vaccine is administered with the cytokine GM-CSF.

12. The anti-tumor composition of claim 1, wherein the vaccine comprises irradiated autologous medulloblastoma tumor cells previously infected with the Zika virus.

13. The anti-tumor composition of claim 12, wherein the vaccine is administered with the cytokine GM-CSF.

14. The anti-tumor composition of claim 1, wherein the vaccine comprises irradiated allogeneic medulloblastoma tumor cells previously infected with the Zika virus.

15. The anti-tumor composition of claim 14, wherein the vaccine is administered with the cytokine GM-CSF.

16. The anti-tumor compositions of claim 1, wherein the target tumor cells express the receptors AXL receptor tyrosine kinase, dendritic cell-specific intercellular adhesion molecule-3-grabbing non-integrin (DC-SIGN), T-cell immunoglobulin and mucin domain 1 (TIM-1), tyrosine-protein kinase receptor TYRO3, or any Zika-virus-associated receptor.

17. A method of treating an intracranial tumor of a subject, comprising the steps of (a) obtaining an anti-tumor composition comprising Zika virus and a carrier suitable for direct intra-tumoral delivery, (b) delivering the anti-tumor composition to the intracranial tumor, and (c) administering a tumor vaccine comprising irradiated autologous or allogenic tumor cells previously infected with the Zika virus to the subject, wherein the tumor vaccine specifically target the intracranial tumor such that the subject's tumor is treated.

18. The method of claim 17, wherein the delivery of the Zika virus is via injection.

19. The method of claim 17, additionally comprising the step of treating the patient with multiple doses of the tumor vaccine.

20. The method of claim 17, wherein the vaccine additionally comprises GM-CSF or IL-12.

21. The method of claim 17, wherein the tumor vaccine comprises irradiated autologous or allogenic GBM tumor cells or medulloblastoma tumor cells previously infected with the Zika virus.

22. The method of claim 17, wherein the delivery of the virus into the intracranial tumor comprises delivering irradiated Zika virus or irradiated cells previously infected with the Zika virus.

23. The method of claim 17, wherein delivery of the Zika virus and the vaccine are in separate doses.

* * * * *

UNITED STATES PATENT AND TRADEMARK OFFICE
CERTIFICATE OF CORRECTION

| | | |
|---|---|---|
| PATENT NO. | : 11,406,697 B2 | Page 1 of 1 |
| APPLICATION NO. | : 16/808701 | |
| DATED | : August 9, 2022 | |
| INVENTOR(S) | : Walter C. Low et al. | |

It is certified that error appears in the above-identified patent and that said Letters Patent is hereby corrected as shown below:

In the Specification

Column 20, Line 54, "Mill" should be --MRI--.

Column 20, Line 58, "MM" should be --MRI--.

Column 27, Line 29, "MEW" should be --MHC--.

Column 35, Line 63, "Banal" should be --Barral--.

Column 37, Line 35, "Lane" should be --Larre--.

Column 38, Line 12, "ALKBHS" should be --ALKBH5--.

In the Claims

Column 39, Claim 17, Line 13, "target" should be --targets--.

Signed and Sealed this
Eleventh Day of October, 2022

*Katherine Kelly Vidal*

Katherine Kelly Vidal
*Director of the United States Patent and Trademark Office*